United States Patent
Wick

(10) Patent No.: US 6,485,686 B1
(45) Date of Patent: *Nov. 26, 2002

(54) METHOD AND APPARATUS FOR COUNTING SUBMICRON SIZED PARTICLES

(75) Inventor: Charles Harold Wick, Darlington, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/662,787

(22) Filed: Sep. 15, 2000

Related U.S. Application Data

(60) Provisional application No. 60/154,592, filed on Sep. 17, 1999.

(51) Int. Cl.$^7$ ............................................. G01N 9/30
(52) U.S. Cl. .................. 422/72; 422/82.01; 422/100; 422/101; 422/102; 73/61.72; 73/865.5; 73/28.04; 435/5; 435/287.1; 435/308.1; 435/309.1
(58) Field of Search .................. 422/72, 82.01, 422/102, 100, 101; 73/61.72, 865.5, 28.04; 435/239, 5, 287.1, 309.1, 308.1; 210/102

(56) References Cited

U.S. PATENT DOCUMENTS

| | | | |
|---|---|---|---|
| 4,217,418 A | * 8/1980 | McAleer et al. | 435/239 |
| 5,076,097 A | * 12/1991 | Zarrin et al. | 73/61.72 |
| 5,247,842 A | * 9/1993 | Kaufman et al. | 73/865.5 |
| 5,606,112 A | * 2/1997 | Flagman et al. | 73/28.04 |
| 5,645,715 A | * 7/1997 | Coombs | 210/94 |
| 6,051,189 A | * 4/2000 | Wick et al. | 422/82.01 |
| 6,254,834 B1 | * 7/2001 | Anderson et al. | 422/102 |

* cited by examiner

Primary Examiner—Jill Warden
Assistant Examiner—Brian Sines
(74) Attorney, Agent, or Firm—Ulysses John Biffoni; William W. Randolph

(57) ABSTRACT

A system for detecting the presence of different size groups of submicron size particles in a fluid sample collected from the environment includes apparatus for collecting the environment. The collected a liquid sample containing submicron size particles selected from the group of viruses, prions, macromolecules, proteins and satellites, is directed to an electrospray assembly having an electrospray capillary for ejecting droplets of the fluid sample under the influence of an electric field. The ejected droplets from the electrospray assembly are directed to a differential mobility analyzer which passes the ejected droplets through an electric field, and the particles are then directed to a condensation particle device for counting the number of particles that pass through the electric field.

20 Claims, 26 Drawing Sheets

FIG. 3

(Graph: AEROSOL CONCENTRATION [p/cc] vs DIAMETER (nm), with x-axis values 1.5, 2.2, 3.0, 4.2, 5.8, 8.0, 11., 15., 21., 29., 40. and y-axis from 0 to 400)

FIG. 4

MS2 PHAGE (Graph: AEROSOL CONCENTRATION [p/cc] vs DIAMETER [nm], x-axis logarithmic from 1 to 100, y-axis from 0 to 4000)

FIG. 7

| Legend | Virus family | Range of density, size | Preferred range of density, size |
|---|---|---|---|
| B | Adenoviridae | 1.30-1.39, 67-115 | 1.32-1.35, 80-110 |
| C | Arenaviridae | 1.18-1.25, 45-300 [1.27-1.36, 40-290] | 1.19-1.24, 50-150 |
| D | Astroviridae | 1.35-1.44, 26-32 | 1.35-1.40, 27-31 |
| E | Caliciviridae | 1.32-1.45, 28-40 | 1.33-1.40, 29-39 |
| F | Coronaviridae | 1.18-1.26, 80-170 [1.25-1.33, 100-160] | 1.23-1.25, 120-160 |
| G | Filoviridae | 1.30-1.40, 75-400 [1.32-1.39, 70-390] | 1.31-1.34, 80-230 |
| H | Hepadnaviridae | 1.23-1.30, 30-45 [1.33-1.38, 24-40] | 1.24-1.26, 34-42 |
| I | Herpesviridae | 1.19-1.33, 90-200 [1.25-1.35, 90-180] | 1.20-1.30, 100-180 |
| J | Orthomyxoviridae | 1.18-1.26, 75-125 [1.25-1.34, 65-110] | 1.19-1.26, 80-120 |
| K | Papovaviridae | 1.19-1.36, 35-57 | 1.31-1.34, 40-55 and 1.19-1.24, 37-42 |
| L | Paramyxoviridae | 1.18-1.27, 100-300 [1.25-1.33, 90-280] | 1.18-1.26, 130-200 |
| M | Retroviridae | 1.15-1.24, 70-120 [1.24-1.29, 70-95] | 1.17-1.23, 80-100 |
| N | Flaviviridae | 1.14-1.28, 30-65 [1.25-1.32, 30-55] | 1.20-1.26, 40-60 |
| O | Parvoviridae | 1.38-1.45, 17-27 | 1.38-1.42, 18-26 |
| P | Picornaviridae | 1.30-1.46, 20-30 | 1.31-1.44, 22-30 |
| Q | Poxviridae | 1.28-1.35, 140-370 [1.29-1.38, 130-360] | 1.29-1.33, 150-350 |
| R | Togaviridae | 1.17-1.27, 60-85 [1.24-1.33, 58-70] | 1.19-1.25, 65-80 |
| S | Bunyaviridae | 1.15-1.24, 80-130 [1.25-1.30, 70-110] | 1.19-1.22, 80-120 |
| T | Reoviridae | 1.35-1.43, 55-85 | 1.36-1.39, 65-85 |
| U | Rhabdoviridae | 1.17-1.23, 45-300 [1.20-1.27, 40-290] | 1.18-1.21, 50-220 |

METHOD AND APPARATUS FOR COUNTING SUBMICRON SIZED PARTICLES

CROSS-REFERENCE TO RELATED APPLICATIONS

This application claims the benefit of priority of U.S. Provisional Patent Application serial No. 60/154,592 filed Sep. 17, 1999, herein incorporated by reference, which is co-pending with related U.S. patent application Ser. No. 08/941,990, now U.S. Pat. No. 6,051,189.

GOVERNMENT INTEREST

The invention described herein may be manufactured, licensed, and used by or for the United States Government. The invention also relates to U.S. Pat. No. 6,051,189, assigned to the United States Government.

BACKGROUND OF THE INVENTION

1. Field of the Invention

The present invention relates to the detection, identification and monitoring of submicron size particles. More particularly, the invention pertains to apparatus and method for the automated detection, identification, and monitoring of submicron size particles. Preferably, the present invention provides for the sampling, detection and identification of viruses and virus-like agents (such as, for example, prions, viral subunits, viral cores of delipidated viruses, etc.) in bioaerosols and fluids.

2. Brief Description of the Related Art

Detection and identification of viruses without limiting the detection and identification to a particular family, genus and species and searching for viruses pathogenic to humans in a single environment is difficult.

The difficulty of detecting and monitoring a wide range of viruses also varies by environment, but perhaps a most troublesome environment involves combat conditions, such as a potential biological warfare (BW) threat environment. Notwithstanding the variation in virulence from virus to virus, in general the ingestion of $10^4$ virions constitutes a significant threat to a soldier who breathes on the order of 1,000 liters (1 $m^3$) of air per hour. Instruments are needed with sensitivities which enable detection of remote releases of biological agents in a field environment thereby providing early warning capabilities, allowing calculations for troop movements and wind patterns.

Additionally, it has been difficult to maintain a broad-spectrum system for the detection of viruses which are free from false negatives because of natural or artificial mutations. Consideration should be given to the high mutation rates of known viruses, the emergence of new viruses, such as the Ebola virus, and the potential for deliberate artificial mutations of viruses. Furthermore, there are virus-like infectious agents, such as prions, which are suspected of causing scrapie, "mad-cow disease" and Creutzfeldt-Jakob disease. These prions possess no DNA or RNA, and can withstand 8 MRads of ionizing radiation before losing infectiousness. Other virus-like infectious agents, such as satellites, possess no proteins.

In the detection and monitoring of viruses recognition should be given to false positives associated with background materials. Background includes biological debris which obscures the detection of the viruses by registering as a virus when a sample is analyzed. Analysis of viruses requires a very high degree of purification of those viruses to overcome background loading in order to avoid false positives. For example, a BW virus may be buried within loadings of other microorganisms which form biological debris having loading on a magnitude of $10^{10}$ larger than the threshold loading for the targeted virus itself Although methods that culture viruses can often be used to increase the virus over background, culture methods may be too slow for effective viral BW detection; futhermore, some important viruses cannot be easily cultured.

As set forth in U.S. Pat. No. 6,051,189 assigned to the U.S. Government and herein incorporated by reference, viruses may also be extracted from an environment and concentrated to an extent that permits detection and monitoring of viruses, without culturing procedures. Generally, in the detection of small amounts of viruses in environmental or biological liquids, it is necessary to both enrich the concentration of viruses many orders of magnitude (i.e., greatly reduce the volume of liquid solubilizing the viruses) and accomplish removal of non-viral impurities. In the presence of non-viral impurities, even the most sensitive detection methods generally require virus concentrations on the order of 10 femtomoles/microliter or more in the sampled liquid to reliably detect the viruses.

Sampling for airborne viruses is generally accomplished by collecting airborne particles in liquid, using a process such as air scrubbing, or eluting from filter paper collectors into a liquid medium. Collection and subsequent separation and detection methods are affected by the adsorption of viruses into solids in aerosols and liquids.

In contrast, when sampling liquids for viruses, in many cases no special equipment or processes may be necessary in order to collect a sample; for example, in sampling blood and other body fluids for viruses, only a standard clinical hypodermic needle may be needed. For sampling of bodies of water or other conveniently accessible liquids, sample collection may not be an issue at all, and in such cases the term "collector" is often applied to what is, in reality, a virus extraction step (such as collection on a filter).

Rapid detection translates into protection for soldiers, more reliable and simplified strategic planning, and validation of other BW countermeasures. Previously known detection methods using biochemical reagents may often be impractical in the field, even for trained virologists. Additionally, reagent-intensive approaches, such as multiplex PCR, low-strigency nucleic acid hybridization, and polyclonal antibodies, may increase the incidence of false positives several hundred-fold, whether under highly idealized laboratory conditions or in the field. Additionally, the hypervariability, or rapid mutation, of viruses and emergence of new, uncatalogued viruses may preclude methods based on biochemical assays, such as PCR, immunoassay, and the like, from achieving broad-spectrum detection of all viruses regardless of identity, known or unknown, sequenced or unsequenced.

SUMMARY OF THE INVENTION

The present invention comprises a system for detecting the presence of different size groups of submicron size particles in a fluid sample collected from the environment. The system includes a collecting apparatus for collecting a fluid sample containing the submicron size particles which include virus and virus-like agents. After the sample is collected, the sample is directed to a means for detecting the submicron size particles, wherein the detection apparatus includes an electrospray assembly having an electrospray capillary, a differential mobility analyzer which receives the output from the capillary, and a condensation particle counter for counting and identifying the submicron size particles in the sample.

Accordingly, one object of the present invention is to detect known and unknown or viruses and virus-like particles which may be pathogenic to humans.

Another object of the present invention is to provide a method and device for rapid detection and identification of viruses which is based on the physical characteristics of viruses.

A further object of the present invention to provide an automated system for the detection and identification of viruses and virus-like agents.

These, together with still other objects of the invention, along with the various features which characterize the invention, are pointed out with particularity in the appended claims.

BRIEF DESCRIPTION OF THE DRAWINGS

Other objects and advantages of the invention will become apparent upon reading the following detailed description with reference to the attached drawings, wherein:

FIG. 3 shows a plot of the GEMMA data for two ultrafiltered samples;

FIG. 4 shows a plot of GEMMA data for MS2 phage for four runs of a known standard sample after ultrafiltration;

FIG. 7 provides a table giving the densities (g/ml) and size (nm) for known viral families containing species pathogenic to man;

DETAILED DESCRIPTION OF THE PREFERRED EMBODIMENTS

The present invention comprises a method and apparatus for the detection and monitoring of submicron particles. The method and apparatus allows for the collection, concentration, purification and detection of viruses that are pathogenic to humans.

Figure 1:
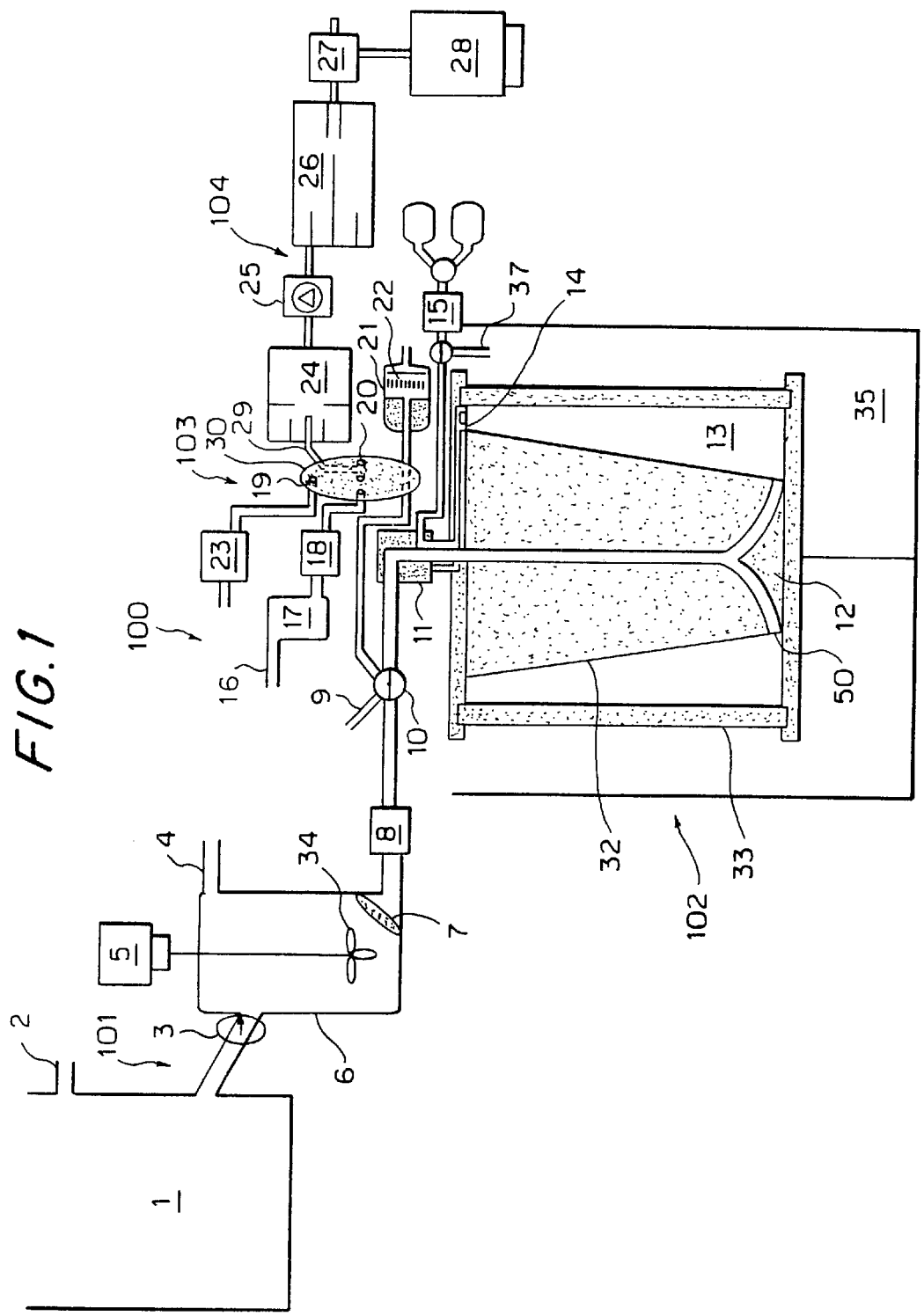
FIG. 1 is a schematic illustration of the integrated virus detection system of the present invention.

As set forth in U.S. Pat. No. 6,051,189 and as shown in FIG. 1, an integrated virus detection system (IVDS) 100 includes a collection stage 101, an extraction stage 102, a purification/concentration stage 103, and a detection stage 104.

In the collection stage 101, a collector 1 is used for aerosol or gaseous fluid sampling. In aerosol sampling, the collector 1 samples airborne particles in the approximate size range of from about 2 to about 10 microns and which may carry viruses and virus-like particles having a size range of from about 10 to about 350 nanometers. Normal collection rates would be from about 100 to about 4,000 liters/min of air. Collection of the submicron size virus particles in the collector 1 is facilitated by the fact that airborne viruses generally travel in or on aerosol particles which measure larger than a micron. In exceptional cases where the virus is not rafting on a supermicron fomite, the danger of transmission by inhalation is generally reduced because of the distribution of submicron particles in the atmosphere and the difficulty in capture by the lungs. The collector 1 has a water inlet 2 which is connected to a water source, such as tap water or a water purification system. The collector 1 scrubs the collected particles with the incoming water from the water inlet 2. Examples of the collector 1 are the U.S. Army's XM2 or the SPINCON collector made by Midwest Research Institute.

In many applications other than aerosol sampling, samples which may contain viruses, for example, are obtained without need for what would be considered a formal "collection stage", such as when the samples are already in the liquid form. These include, for example, blood samples, obtained by ordinary means familiar in clinical settings, as well as other body fluids such as mucus, semen, feces, lymph, saliva, etc. Also in this category are situations involving sampling of bodies of water such as municipal water supplies, rivers and lakes, beverages, and high-purity water used for microelectronics manufacture.

The collector 1 includes tubing 3 which connects the collector 1 to a holding tank 6 containing a blender or homogenizer 5. The collector 1 has an aqueous stream output on the order of 1–10 ml/minute containing the scrubbed particles which is pumped through the tubing 3, preferably of TEFLON or polysiloxane-coated to reduce adsorptive losses. The tubing 3 is connected to a one liter holding tank 6. Alternatively, the tubing 3 can be connected directly to the extraction stage 102 or according to one embodiment of the present invention, directly to a detection stage 104.

In the holding tank 6, solids in the aqueous stream are broken up by using the homogenizer 5, or alternatively, by forcing the aqueous stream through an orifice. The homogenizer 5 has a bladed section 34. Surfactant or amphiphile is added at the inlet 4, which preferably is mixed with water prior to entry into the holding tank 6. The surfactant or amphiphile breaks down the structures in the aqueous stream. Preferably, the amphiphile has a low boiling point, which allows easy removal of the amphiphile in a later stage. Most preferred, the amphiphile is diethylene glycol monohexyl ether. Base is also preferably added to increase the pH of the homogenized liquid which tends to decrease aggregation. Examples of the homogenizer 5 are the Lightnin Closed Tank Model general purpose stirrer model G2S05R, available from Lightnin, a unit of General Signal of Avon, N.Y., catalog no. 869435, or the PC-controllable stirring motor, RE162 analog, ID no. 8000700 and rotor-stator S 50 N-W 65 SK, ID no. 8005100 from IKA Works, Inc. of Cincinnati, Ohio, which serves as part 34.

In leaving the holding tank 6, the aqueous stream passes a screen filter 7 which regulates the output of the holding tank 6. The screen filter 7 is preferably 10 micron mesh and made of stainless steel or other corrosion-free material. A pump 8, which is designed for pumping liquids through the tank 6, draws the aqueous stream from the holding tank 6 and through the screen filter 7.

Beyond the pump 8, a three-position PC-controlled switch 10 is used to allow the discharge from pump 8 to flow into a centrifuge rotor 12 in a first position. To understand the function of the second and third positions of this switch, it is necessary to realize that after centrifugation, the gradient imprisoned in the rotor can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175–1.46 g/ml, as discussed elsewhere herein; alternatively, a subset of this range could constitute the useful range if only certain viruses are being analyzed for.

Thus, the second position of switch 10 allows the useful part of the gradient to flow on to part 30 (in particular, to the first position of part 30, as discussed below), and the third position of the switch allows the discarded portion of the gradient from the rotor 12 to flow out through a port 9; if desired, port 9 can incorporate means to recycle density gradient material, if desired. In the first position, as the screen-filtered sample from the pump 8 travels past the switch 10, it enters into the extraction stage 102.

In the extraction stage 102, the aqueous stream enters a liquid-cooled coaxial seal 11. After passing the coaxial seal 11, the aqueous stream enters at the upper shaft of the rotor 12. The rotor 12 is a zonal ultracentrifuge rotor, such as a Beckman's CF-32 rotor or Z-60 rotor, which is inserted into and spun by a centrifuge 35, such as a Beckman Optima XL-100K Preparative Ultracentrifuge. For large sample volumes with small quantities of viruses, for example monitoring of bodies of water, such as drinking water sources, the present invention preferably uses continuous-flow density gradient ultracentrifugation, using for example the Beckman's CF-32 rotor. For other applications, ordinary zonal centrifugation is preferred with rotor 12 being a Beckman's Z-60 rotor. In a special seal and bearing assembly, fluid inlet and outlet streams access an annular space 13 between a core 32 and rotor wall 33 through the coaxial seal assembly 11 and via port 50. Density gradient solutions, sample liquid, and the displacement fluid are sequentially pumped into the annular space 13. Density gradient solutions are loaded from port 15 through inlet 14. From pump 8, sample liquid is added. A density gradient solution is any liquid which permit the separation of viruses, such as a sucrose or, preferably, cesium chloride solution.

In continuous flow operation, the virus-containing liquid stream is pumped in from the collection stage 101 and flows continuously over the density gradient in the rotor 12, and viruses sediment out of the stream, banding into the density gradient according to buoyant density. This pumping of sample into and out of the rotor 12 can be performed with the centrifuge spinning at high speed. The continuous stream allows a large volume of fluid to flow through the annular space 13, which permits virus material to be captured in the gradient, even with small concentrations of viruses in the fluid. In ordinary zonal operation (not continuous-flow), the sample does not flow continuously into the rotor for long periods of loading, but rather the entire sample volume, which must be less than the annular volume in the rotor, is loaded and enclosed in the rotor 12. The rotor volume is then closed off before acceleration to high speed. In either case, this is called the loading phase of the isopycnic banding separation. After loading and centrifuging to achieve banding, the virus-containing bands are recovered by displacing the bands sequentially, with lowest density bands exiting first and highest density last. As the density of each virus uniquely determines the position of that virus or particle in the exiting stream, the timing of the detection of specific virus particles provides particle density information.

A fresh gradient is loaded into the rotor 12 by pumping a low density fluid, containing no cesium chloride, into the rotor 12. As illustrated schematically by the presence of two fluid tanks and a mixing valve in part 15 of FIG. 1, a high density fluid, typically containing about 60% cesium chloride is mixed with the low density fluid at a variable high:low ratio, which via PC control increases with time until the loading is complete. The fluids pass through the fluid entry ports 14 at the top of the annular space 13. Concurrently, the rotor 12 is spinning at a low speed of about 4,000 rpm, with the speed being controlled by the timer control system in tandem with the fluid entry and displacement.

After the fresh gradient is loaded, the control system actuates valves which flow fluid through the rotor 12 in the opposite direction, pumping sample from the holding tank 6, through switch 10 (in the first position), through the bottom entry port 50, and upward through the annular space 13, entering at the bottom end and displacing fluid out at the top of the rotor 12 through 14 and out discharge port 37. After establishing flow reversal, the control system initiates and regulates the centrifuge to a preferred rotational speed of about 60,000 rpm for a B-series rotor. In extremely dry environments, water exiting the centrifuge may be recycled back into the system by pumping it back into the collector 1 where it can be used for air scrubbing. At a rotational rate of 60,000 rpm and flow rate as high as 6 liters/hr, over 90% of all virus enters the g where it remains imprisoned. After on the order of 10–30 minutes of operation, which allows as much as 3 liters of sample fluid to pass through the rotor 12, the inflow and effluent flow are shut off, and the high-speed rotation continues for an additional 30 minutes to band the viruses. The viruses become banded in the gradient. The centrifuge controls are actuated by a timer-regulated control system, which is preferably a standard PC-computer interface.

In operation, sample liquid is introduced into the density gradient within the centrifuge rotor at the low-density end of the gradient, and each particle or molecule penetrates into the gradient at a rate that increases with the mass of the particle, and with the density. In the case of a protein molecule, the mass is much smaller than that of a virus by at least an order of magnitude, and the density is about the same as that of a relatively low-density virus. Accordingly, the rate of banding for proteins is much slower than for viruses. The centrifugation is run just long enough for the smallest virus particles of interest to have enough time to band to the desired resolution in the gradient. This is typically within about 1–5% of the equilibrium position. The proteins will then primarily be to the low-density side of their equilibrium positions, as they started on that side. Since the equilibrium position of most proteins in a gradient is nominally about 1.3 g/ml, at the end of this shortened operating time, most proteins are positioned considerably lower than 1.3. The proteins are at positions which are not collected, and not sent on to the next stage as they are outside of the "virus window". Accordingly, the density-gradient centrifugation step takes on some of the properties of a combined two-stage density-gradient/sedimentation coefficient separation.

Once the viruses are banded, the centrifuge is decelerated to low speed, and the gradient is recovered by pumping the dense fluid of preferably 60% CsCl from the gradient supply system 15 to the outer edge of the annular space 13 through 14. The dense fluid displaces the gradient, with low density bands exiting first followed by high density bands. After gradient removal, the high density material in the rotor 12 is displaced by low density fluid, which enters from the inner rim of the annular space 13 at point 50 and displaces the high density material from the outer edge of the annular space 13. The procedure is complete in a few minutes, and the cycle repeats again beginning with the loading of the density gradient at low speed.

Ultracentrifugation provides the advantages of desorption of viruses from fomites and universal capture of all catalogued and non-cataloged viruses, with high capture efficiencies of greater than 95%. Ultracentrifugation also is not dependent on biochemical reagents, and provides a high degree of virus separation from the background components. Additionally, density information of the viruses is provided by the ultracentrifugation, providing the y-coordinate in the Virus Window plot, discussed herein. The coaxial seal 11 is commercially available as a Beckman's Zone Assembly, part no. 334241. Examples of the centrifuge rotor are the U.S. Army's B-VIII, B-IX and B-XVI, or preferably the Beckman Spinco CF-32 Ti Continuous Flow Rotor, or Beckman's Z-60 rotor for ordinary zonal centrifugation. For the centrifuge itself, the Beckman Optima XL-100K Preparative Ultracentrifuge is well-suited for all of these rotors.

Figure 6:
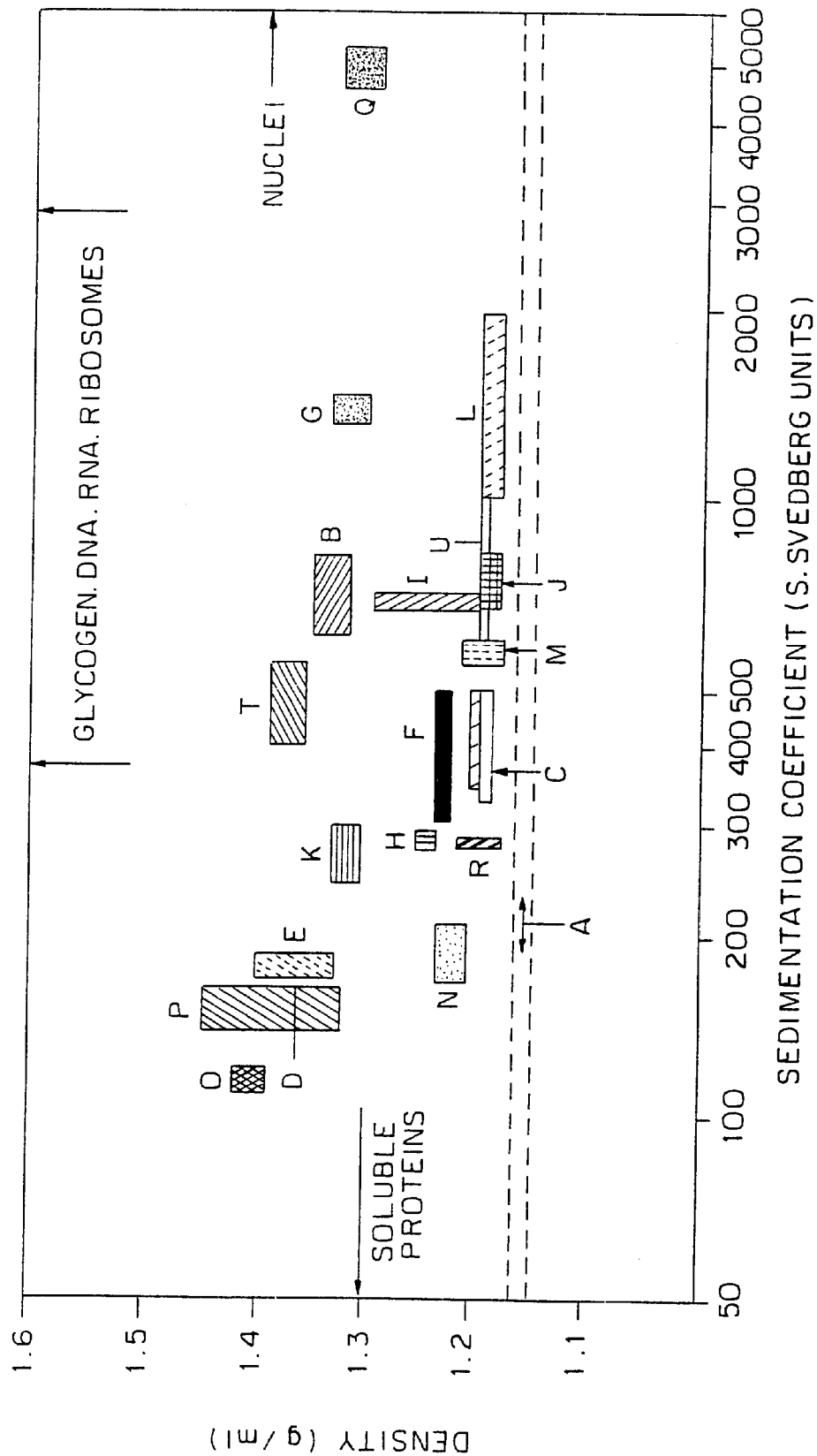
FIG. 6 is a plot of the virus window showing the densities and sedimentation coefficients for viruses pathogenic to man.

The results of the extraction of the ultracentrifugation of the centrifuge rotor 12 are analyzed from biological background by means of a "Virus Window". The Virus Window is a density-size (r-d) or density-sedimentation coefficient (r-S) plot of biological components which are pathogenic to humans, with the x-axis showing either size d or sedimentation coefficient S, and the y-axis showing density r, as shown in FIG. 6. Mammalian viruses are approximately between 1.175 and 1.46 gm/ml density and have a diameter between about 22 and 200 nanometers (or, alternatively rephrasing this size range, with sedimentation coefficient between 120 and 6,000 Svedberg units). The Virus Window is an extremely useful concept not only because it shows how viruses can be separated from other non-viral background, but also because the different virus families are substantially separable from each other. Within the Virus Window, each virus family is distinguished by a particular rectangle with little overlap between the 20 family rectangles. Accordingly, with a known density and size, the detected virus particle is pinpointed to its particular family in the Virus Window. In any case, particles with densities and sizes that both fall in the Virus Window ranges can, with high confidence, be presumed to be viruses; thus when counts are registered in the detector of the present invention, having previously been selected by centrifugation for density in the range of about 1.175 to 1.46, and further selected by the Differential Mobility Analyzer for size between about 22 and 200 nm, then it can be concluded with a high degree of confidence that these indicate the presence of viruses in the sample. Furthermore, this confidence level is further increased if the density and size fall into a particular region of the Virus Window known to correspond to a virus. Similarly, other particles of potential interest in detection—such as prions, other virus-like particles, and other natural or artificial particles, colloids, cell structures, or macromolecules—will frequently have unique positions in the density-size plot that may allow them to be separated from other components and thereby be detected in the present invention.

Although to a very large degree only pathogenic viruses fall within the Virus Window, other background components fall close to the Virus Window. These components are microsomes and similar sub-cellular structures. These components can be effectively eliminated by adding nonionic surfactant, such as diethylene glycol monohexyl ether, to the collection stage 101 exit stream at inlet 4. The surfactant solubilizes the microsomes and membrane fragments. As recovery of viable viruses is not necessary, release agents can be used. The release agents are preferably organic solvents and surfactants, more preferably amphiphiles, and most preferably low molecular weight amphiphiles such as diethylene glycol monohexyl ether. The release agents provide several useful effects. First, they act to break up and even dissolve cellular substructures, such as microsomes, ribosomes, lysosomes, peroxisomes, and mitochondria, which have sizes and densities similar to viruses and set the limit on the required resolution, in the case of detection of viruses. Second, upon dissolution of the lipid envelope with such agents, the increase in the virus density is significant (the density of the viral core, which is the virus minus its lipid envelope, is in general significantly higher than that of the enveloped virus). In the case of hepadnaviridae, for example, this may be from about 1.25 to 1.36. Both effects serve to further differentiate viruses from, particularly, microsomes in the Virus Window plot, the first by acting to eliminate the microsomes, and the second by increasing the difference in density between the viruses and the background microsomes. Third, release agents enhance the desorption of viruses from solid matter, which is particularly important in the detection of airborne viruses. Release agents can also break up aggregates of viruses, especially aggregates of encapsulated viruses. The present invention minimizes this aggregation problem in other ways besides the use of release agents. The centrifugation can be performed without pelleting. Consequently, buoyant density, and thus isopycnic banding, is not greatly affected by aggregation under these circumstances. (Indeed, banding times are favorably reduced in the case of aggregation, and techniques can be applied that take advantage of this, within the broad context of the present invention). Any aggregation will generally produce only a small shift in, and/or broadening of, resulting virus bands. The portion of this exiting stream that contains the Virus Window is pumped to the purification stage 103 with the position of a particle along this stream giving the density of that particle. The useful part of the stream, in the case of general virus detection where the range 1.175–1.46 is passed to the next stage, is in the preferred embodiment on the order of about 10 ml; thus, this stage does not effect a large increase in virus concentration, though it does effect a very large increase in the concentration of viruses relative to other non-viral components.

Although feasible, a separate centrifugation to separate particles by sedimentation coefficient for Virus Window x-coordinate information is not necessary. A Differential Mobility Analyzer (DMA) 26, which as described below, provides rapid analysis of particle size. Additionally, separation of viruses from soluble proteins can also be done in the purification stage 103. An even further separation of proteins, and other macromolecules smaller than viruses, from viruses can also be done by tuning the supersaturation in a condensation particle counter so as to not detect macromolecules as small as proteins. The centrifuge dimension and rotor speed for optimal centrifugation can be calculated. Optimal times are preferably thirty minutes or less and resolutions are preferably 0.02 density units (0.02 gm/ml) or better.

The sample fluid passes from the extraction stage 102 into the purification stage 103. Typically, this could be in the form of 15 pulses, each on the order of 1–10 ml in volume, and each corresponding to a density slice with a width on the order of 0.02 gm/ml. In the purification stage 103, a membrane filter 22 separates the viruses from soluble proteins (removing the need for a second, sedimentation rate centrifugation in the previous extraction stage 102), and concentrates particles with sizes greater than the pore size into a very small volume of liquid; additionally, in this stage soluble salts, including those from the sample as well as the density gradient material (e.g., cesium chloride), are greatly reduced in concentration. The membrane filter 22 may be Millipore's VIRESOLVE Membrane, an AMICON P membrane, or preferably a Pall FILTRON OMEGA Series membrane with a 1,000,000 molecular weight cutoff. The water permeability of the membrane filter 22 is on the order of 0.01 ml/cm2-sec-psi, so that a membrane area of 0.1 cm2 yields a flux of order 6 ml/min at 100 psig transmembrane pressure. The membrane filter 22 is incorporated into a housing which is designed to allow flow rates on the order of 0.1–20 ml/min during filtration, which results in loading of the filter with particles larger than about 15 nm (which includes all virus particles), after which the particles are confined within a small front-face-side collection volume. A small-volume filtration filter holder 21, such as Schleicher & Schuell's SELECTRON, is used to hold the membrane filter 22. More preferably, a filter holder with a design like that of the SELECTRON, but made out of an alternative material which does not degrade electrolytically under high voltage, is used.

A four-way positioner 30 in the purification stage 103 allows automated processing of particles in the membrane filter 22. The positioner 30 is driven by a computer-controlled motor which positions the filter holder in one of four ports.

In the first position, the positioner 30 positions the membrane filter 22 to accept the sample flow outputted from the extraction stage 102. Each 0.02 gm/ml density slice from the output of the extraction stage 102 is, after passing through switch 10 in the second position, loaded through the membrane filter 22 in less than about 2 minutes; alternatively, larger density slices can be filtered, requiring appropriately longer times. A standard 0.2 micron poresize filter (such as available from Corning Costar) is preferably incorporated in the connection between the output from 102 and the input to 103, in order to remove any remaining particles greater than about 200 nm in size.

When the positioner 30 is switched to the second position, a valve closes off the sample flow and CsCl-free water from pump 18 out of tank 17 which has an inlet 16 is passed across the membrane filter 22 using on the order of 5 ml of water with a flux time of order 1 minute. This reduces the 30% CsCl aqueous solution surrounding the particles to less than 100 ppm CsCl, and allows recovery of the CsCl for recycling. Additionally, the amphiphile, viscosity additives and buffer components are reduced in the membrane filter 22. More preferably, ammonium acetate solution, with on the order of 20 mM concentration in water, is used for this operation, preparing the liquid for downstream detector stage operation.

On switching the positioner 30 to the third position 19, the pure water (or ammonium acetate solution) is shut off, and a final filtration is performed in order to reduce the volume of liquid on the retentate side of the membrane, thereby greatly increasing the concentration of viruses and reducing the volume of liquid to the small quantities required for operation of the detection stage 104; the filtrate in this step passes out through port 23. More precisely, the purification stage 103 is integrated with the electrospray assembly 24 of the detection stage 104 by a punctured disk fitting. The fitting has a 150 micron hole drilled through a tubular stub in its center. When positioner 30 is in the third position, this hole allows the filtrate to pass out through port 23. When the positioner 30 is in the fourth position, the inlet end of the electrospray capillary 29 (the end opposite the spray tip) is inserted into this 150 micron hole. This fits in a piston-like manner into the stainless steel cylinder of the SELECTRON (or SELECTRON-like) filter holder. The cylinder slides over the steel disk, and is positioned with a gap between the steel disk and the ultrafilter surface on the order of 100 microns.

In the fourth position 20, in accordance with the above, the membrane filter 22 is positioned for entry of the virus containing retentate into an electrospray capillary 29 of the detection stage 104. (Alternatively, instead of fluid passing directly from the purification stage 103 to the electrospray, an intermediate component may be used to accomplish a further purification and/or concentration). A platinum wire may be run from the voltage source of the electrospray unit 24 to the interior of the liquid inside the volume on the retentate side of the membrane filter, in order to establish a current return for the electrospray operation.

The detection stage 104 accomplishes several functions, which include a final purification, an individual virus particle count and a size determination of the detected particles. The detection stage 104 includes three major components, an electrospray assembly (ES) 24, a Differential Mobility Analyzer (DMA) 26 and a Condensation Nucleus Counter (CNC) 27, which is alternatively called a Condensation Particle Counter (CPC). The components may be commercially obtained individually from TSI, Inc. of St. Paul, Minn. The Condensation Nucleus Counter 27 and Differential Mobility Analyzer 26 units are also available commercially from TSI as a single integrated unit, which can be accompanied by an IBM PC with associated software. This allows for an inexpensive set up compared to a mass spectrometer. The detection stage 104 can conduct measurements concurrently with the collector 1 obtaining the next cycle's collection.

Passing from the purification stage 103, the retentate enters the detection stage 104 at the inlet of the electrospray capillary 29 of the electrospray assembly 24 in the fourth position of the positioner 30. Entry into the electrospray capillary 29 is done without passing the retentate through piping, which might cause sample losses. The electrospray capillary 29 is on the order of 25 cm in length, and the inlet of the electrospray capillary 29 is positioned to the small front-face-side collection volume of the UF membrane 22, as described above. The electrospray capillary 29 is then positioned to sample liquid from the retentate-side of the filter and the sample liquid enters the electrospray assembly 24.

In the electrospray assembly 24, the liquid sample solution is passed into an orifice or "jet" of 50 micron diameter, and droplets are ejected under the influence of an electric field. The droplets are typically between 0.1 and 0.3 microns in size, with a fairly narrow size distribution. At a droplet size of 0.3 micron, sampling rates are 50 nl/min (50 nanoliters/minute), allowing the electrospray assembly 24 to spray the collection volume in on the order of 20 minutes per microliter.

From the electrospray assembly 24, the sample passes to a charge neutralizer 25. The charge on the droplets is then rapidly recovered using an ionizing atmosphere to prevent Rayleigh disintegration. The neutralized ES droplets are then dried in flight, leaving the target virus molecules and/or dried residue of soluble impurities. From the charge neutralizer 25, the target virus molecules and/or dried residue enters the Differential Mobility Analyzer 26.

The Differential Mobility Analyzer 26 uses electrophoretic mobility of aerosol particles to classify the particles by size, using the inverse relationship between the mobility of a particle to its size. In the Differential Mobility Analyzer 26, particles are carried by an air stream at a set velocity through an electric field created by a charged rod. If the particle is singly and positively charged, it experiences an electrostatic attraction to the rod, which competes with the inertial force of the flow. When the electrophoretic mobility falls in a certain range, the particles pass through a narrow exit port at the end of the charged rod. The particle size range, which is generally 0.01 to 1 micron, is divided into 147 size channels. The entire range is automatically scanned in 1 to 10 minutes, generally 3 minutes. The Differential Mobility Analyzer 26 has only a possible 3% instrumental error for virus size determination. Additionally, there is a possible size increase due to the covering of the virus particle with impurity residue, which at an impurity level of 100 ppm, a typical 40 nm virus has a possible error of up to about 2% in effective size. If the impurity levels are less than 20 ppm, the error becomes smaller than 1%.

When the primary droplets from the electrospray assembly 24 are 0.3 micron, a 1 ppm soluble impurity creates a 3 nm residue particle, and a 125 ppm soluble impurity creates a 15 nm particle. Particles which are 15 nm in diameter can be separated in the Differential Mobility Analyzer 26 from viruses which are at least 22 nm in diameter. Accordingly, soluble impurities must be reduced to less than 100 ppm (0.01%) to avoid background interference with virus signals.

Detection of proteins at levels of 1011–1012 molecules/ml indicates that a sensitivity level for viruses of 1010 particles/ml can be achieved, and possibly 109 particles/ml, particularly by combining the Differential Mobility Analyzer 26 selection with an adjustment of the Kelvin radius of approximately 10 nm. Impurities of 1 ppm yields a 3 nm residue particle which can overlap protein sizes. Impurity levels of 100 ppm or less are acceptable in the detection of viruses, since viruses are several times larger than proteins. Sensitivities of 1010 molecules/ml and possibly 109 molecules/ml are projected based on documented results using proteins. In one of the Examples given below, detection of 1012 pfu/ml (a pfu is a plaque-forming unit) was easily accomplished even after dilution by a factor of 128, demonstrating detection at a level of 1010 pfu/ml.

The Differential Mobility Analyzer 26 validates against false positives by changing the dilution and seeing whether the particle size also changes. Additionally, the Differential Mobility Analyzer 26 can be used to provide another layer of protection against interference from impurities up to the 100 ppm level. The level of 1010 molecules/ml corresponds to 2×107 viruses in a 2 microliter collection volume of the purification stage 103, and 109 molecules/ml corresponds to 2×106 viruses. At a collection volume of 107 viruses of the present invention, or 20 minutes of XM2 sampling, 20,000 liters (20 m3) of air are sampled. Accordingly, the sensitivity of the present invention is on the order of 500 viruses per liter of air. With impurity levels of 100 ppm or less, virus size can be determined by the Differential Mobility Analyzer 26 to within about 4%. The detection stage requires on the order of 5 to 40 minutes, including Differential Mobility Analyzer 26 size determination, and can be preformed concurrently with centrifugation for a subsequent cycle.

From the Differential Mobility Analyzer 26, the sample enters the Condensation Nucleus Counter 27, which uses a nucleation effect. The aerosol sample enters and passes through a heated conduit having an atmosphere which is saturated in butanol. The sample is routed into a cooled condenser, where butanol vapor condenses onto the sample particles, which act as nuclei. The saturation is regulated so that no condensation occurs on the nuclei below a critical size, which limits false background counts to less than 0.01 particle/ml. With nucleating particles, condensed droplets grow to micron size and are optically detected using a 780 nm laser diode with photodetector. Provided that the level of impurities is low enough that the residue particles are below the threshold of detection by the Condensation Nucleus Counter 27, and/or are separated from the target molecules by size, then only the target molecules will be registered with the Condensation Nucleus Counter 27. As the nucleation of droplets does not depend on surface characteristics of the particles, butanol saturation can be adjusted for a critical size of 0.01 micron radius which minimizes background counts from proteins and other soluble impurities. Response times for step changes in concentration are less than 20 seconds, and operation of all components is in the temperature range from 10° C. to 38° C. Supersaturation tuning for a 10 nm Kelvin radius threshold in the Condensation Nucleus Counter 27 can be used to cancel the detection of non-viral impurities, including proteins, provided they are below about 100 ppm.

The purification stage has an output volumetric rate which is very well suited for input into the ES-DMA-CNC particle counter, which addresses the strict requirements and narrow range of operating parameters for the ES-DMA-CNC unit. In recognizing the high value of this molecule-counting and molecule-sizing ES-DMA-CNC unit, filtration provides excellent samples for the purification/concentration stage prior to this detector. The ES-DMA-CNC combination allows particles to be sized and permits improved sensitivity by an order of magnitude over a DMA-CNC combination. Protein concentrations of 10 mg/ml, or 1011–1012 molecules/ml, can be detected and sized.

The system is controlled by a computer 28. When data collection and instrument control are handled by the same computer, the computer may vary the mode of operation in response to virus detection. Initially, before viruses have been detected, the system places the entire 300 ml of density gradient from the extraction stage 102 through the membrane filter 22 to scan all virus sizes from 22 to 200 nm. Alternatively, the Differential Mobility Analyzer 26 is by-passed entirely, provided that non-viral concentrations are low enough that tuning of the Kelvin radius in the Condensation Nucleus Counter 27 is sufficient to reduce background. Once viruses are detected, the Differential Mobility Analyzer 26 indicates the sizes of the viruses detected. The computer can then trigger the output of the extraction stage 102 to be sampled piecewise in the purification stage 103. By breaking the range of virus densities, which is about 0.3 gm/ml into 10 or 15 slices, the density of the detected virus is within about 0.02–0.03 gm/ml, which is sufficient to narrow most viruses down to a single family. Following this, the region in the centrifuge output stream surrounding this density can be divided still finer, to provide better accuracy on the viral density. Through data base comparison, the system identifies the viral families from the measured densities and sizes, and provides output of detected viruses by density, size, concentration, apparent changes in concentration over time, and if desired, audible and/or visual alarms in the presence of detected viruses. Being automated, the instant invention can run continuously for long periods of time without an operator. In addition to making continuous virus monitoring possible at a large number of sites simultaneously without the need for scores of virologists, the automation afforded by the present invention also limits the risks of viral infection of technicians.

Other potential physical means of separating viruses and other particles from background and/or enriching their concentration may involve capillary electrophoresis (purification and concentration enrichment), sedimentation-rate centrifugation (primarily purification), hydroextraction (mainly concentration), dialysis (purification and concentration), organic/inorganic flocculation (purification and concentration), and capillary chromatography, which can size-exclusion, hydrophobic interaction, or ion-exchange chromatography (purification and concentration).

EXAMPLES

Analysis of two blind samples was performed, using the filter membrane stage and the electrospray (ES)—differential mobility analyzer (DMA)—condensation particle counter (CPC) triage, or gas-phase electrophoretic mobility molecular analyzer (GEMMA).

Filtration: Two samples, labeled as AFO001 and AFO682 were obtained. AFO682 had been collected and contained viruses; AFO001 was a blank or control, although the foregoing was not known about the two samples prior to testing. Each original sample was on the order of 1.2 ml in volume. From each sample, all but about 200 microliters was taken and prefiltered, through a 0.2 micron poresize Millipore syringe filter with low dead volume. Approximately 400 microliters of this was removed in each case and processed in a filtration unit designed and built for this purpose. A 500,000 MW cutoff membrane was selected to separate viruses, which were retained, and to pass proteins and soluble salts out in the filtrate, which was discarded. Successive diafiltration was used, with each filtration step concentrating retained material into a volume of about 5 microliters on the retentate side of the membrane. Between successive filtrations, 20 mM ammonium acetate solution was used to restore the volume to about 400 microliters. This strength of ammonium acetate was used for the proper operation of the electrospray (ES) in the detection stage. After two successive diafiltration steps, two 100 microliter portions of the final, filtered sample were collected in two ways. The first 100 microliters was obtained by forcing out 100 microliters of the retentate volume back through a port which was forward or upstream of the membrane surface, during the final leg of the last diafiltration. This was done after allowing 20 minutes for diffusion of the viruses away from the membrane surface. The second 100 microliters was obtained by using a gas-tight syringe press-fit into the filtrate outlet port, to push ammonium acetate buffer backward across the membrane, from the filtrate side to the retentate side, in order to elute virus from the membrane. The design of the filtration unit was such that the retentate side of the membrane remained in a water environment, avoiding for example, an air-purge or vacuum flush of the system causing irreversible adsorption and breaking of virions.

Detection: The filtration resulted in three 200 microliter samples for each of the two specimens: one before filtering, one prefiltered, and one prefiltered and then ultrafiltered. The samples were placed in Eppendorf vials. Each sample contained ammonium acetate, which is important in maintaining the conductivity necessary for electrospray operation. Being volatile, it decomposes and evaporates into ammonia and acetic acid during the in-flight drying of the electrospray-generated aerosol, and so does not contribute to the final scan. Additionally, each sample contained the viral particles and fragments of interest. Furthermore, each sample contained soluble salts, which are not volatile and thus lead to a "residue particle" after in-flight drying. For example, with the electrospray set at 300 nm droplets, a salt level of 1 ppm would yield an average residue droplet diameter of $(1/10^6)^{1/3} \times 300$ nm=3 nm. Very high salt concentrations can increase conductivity and destabilize the electrospray, which in all the data shown, was not a problem. However, in some scans shown for samples that were not filtered, the salt peak from these residue particles extends out to as high as 15 nm.

Samples were input by inserting a capillary into the Eppendorf vial. Flushes of pure, 20 mM ammonium acetate were run before and between samples. Stability of the electrospray is in general indicated by a current between 200 and 400 nA.

Results: FIGS. 2A and 2B each compare DMA-CNC data for a typical sample before and after ultrafiltration, both being pre-filtered. In each of these two figures, the solid curve shows data before ultrafiltering and the dashed curve after ultrafiltering. In FIG. 2B the peaks centered at about 9.0 nanometers and at about 4.2 nanometers represent background peaks due to soluble impurities (mainly salts) before and after ultrafiltration, respectively.

FIG. 2A, which focuses on the 15–40 nm range where the number of counts is low, show a solid curve for the 'before ultrafiltered', which was diluted by a factor of 16 before running, with a dashed curve for the ultrafiltered sample run at full strength. This plot, which was reproduced over a number of scans, shows the two curves tracking each other well into the region above 15 nm, with the ratio starting well above 1:16 (roughly 1:4) but approaching this at larger diameters. This shows that the ultrafiltration retained this material well, at least as the diameter increased to above 20 nm, but even fairly well between 15 and 20 nm; the MW cut-off curve of the membrane filter rises from 0 to 90+% retention between about 10 and 20 nm., significant since intact virus particles, those lying in families known to be infectious to mammals, are always greater than 20 nm.

Figure 2A:
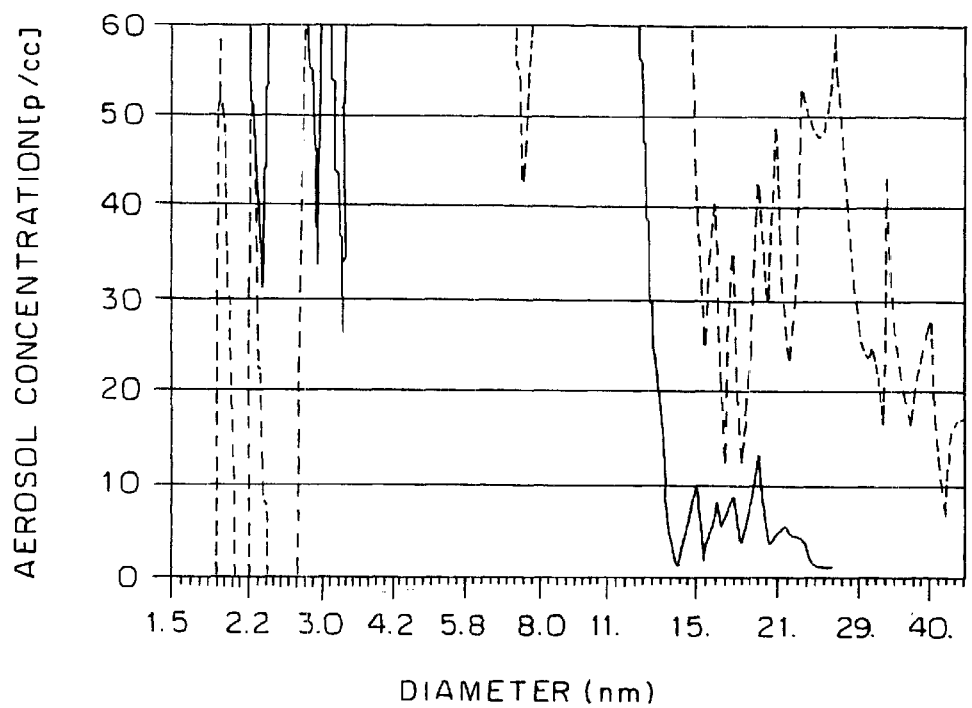
FIGS. 2A and 2B each compare DMA-CNC data for a typical sample before and after ultrafiltration, where the solid curve shows data before ultrafiltration and the dashed curve shows data after ultrafiltration.
Figure 2B:
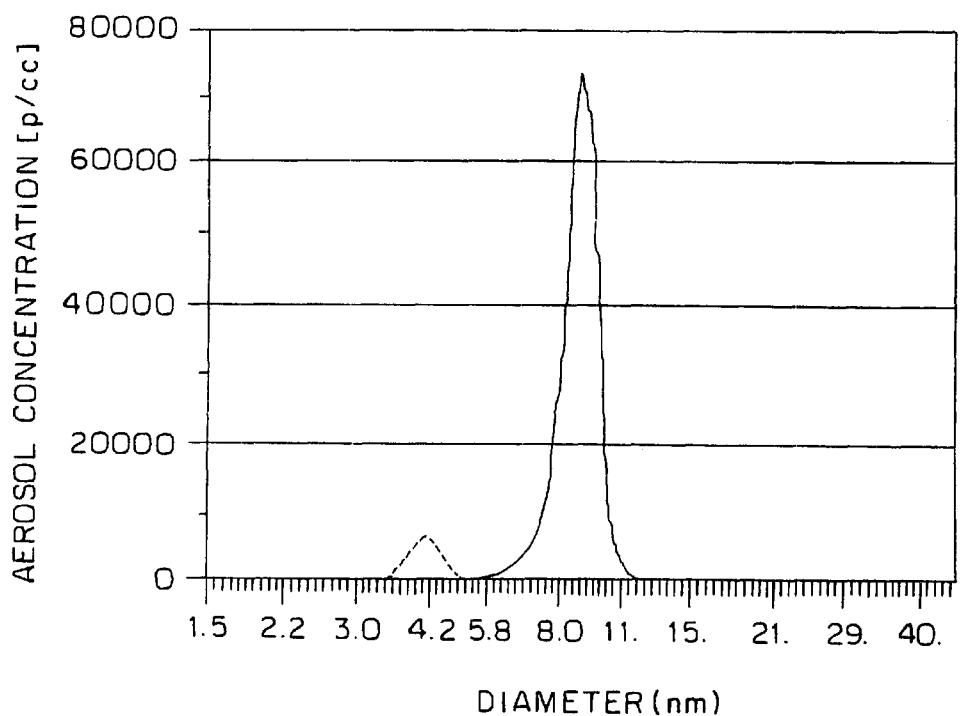
Figure 5:
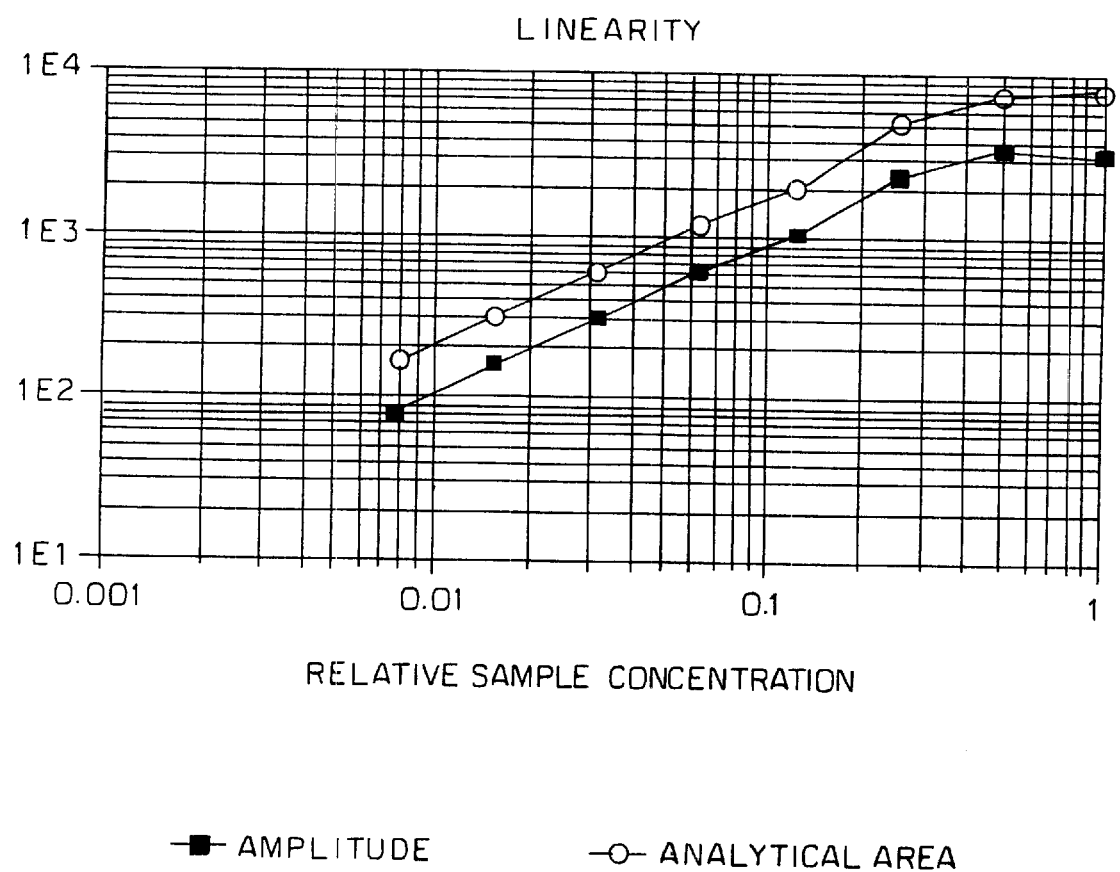
FIG. 5 shows peak amplitudes and areas plotted as a function of successive dilutions of the sample of FIG. 4.

In FIG. 2B, the dashed curve shows data after ultrafiltration in comparison with the solid curve before ultrafiltration. FIG. 2B shows a greatly reduced salt content, given by the cube of the diameter ratio, and remarkable reductions in protein concentrations. The protein concentration are in the range of 7–15 nm, in which many proteins lie, particularly, proteins higher than about 80,000 MW. The data under the solid curve are for the non-ultrafiltered sample at 1/16th strength, so that the reduction is even more dramatic than as appears in the plot. As plot 2A, above, showed that the 15+ nm fraction was preserved by the ultrafiltration, even quantitatively above 20 nm. The reduction in the salt peak was also extremely good, both in intensity and in the lowered diameter, pushing it down away from the region of interest. This indicates that the ultrafiltration methodology is extremely effective for removing soluble salts and proteins, while preserving 20 nm and greater fractions. It is evident that the ultrafiltration reduced the background, which is due to the salt residue particles, both in magnitude and location, shifting the peak position for the background from about 11 nm to about 5 nm, putting it well below the range of interest for virus detection.

The experimental results of an environmental source sample was analyzed with the filter-ES-DMA-CNC combination. As a blinded experiment, the components of the two samples were not known, except that one sample could be a "blank", with no viruses, and the other sample was either doped with virus or was an environmental sample, collected from sampling of air in the wild. Upon analysis of the DMA-CNC data, viruses were detected and counted in one sample, AFO682, and no viruses detected in the second sample.

FIG. 3 shows a plot of the GEMMA data for the two ultrafiltered samples. The x-axis gives the particle size in nanometers, and the Y-axis gives a concentration measurement. Evidence of particles in the range of 22–40 nm was shown, the range for intact virus particles, in sample AFO682. In sample 682, the counts here are quite low, and translated into concentrations on the order of $10^{10}$ particles/ml or 10 femtomoles per ml, after filtering. In sample AFO001, there is essentially no activity measured in the range 22–40 nm, where background counts are typically 0, or at most 8 counts. With isopycnic banding information from the centrifuge stage, a double-check to distinguish between simple protein aggregates or polysaccharides with gravimetric densities of about 1.3 or less, and unenveloped viruses of about 1.4 is possible. Upon use of the full system including centrifuge, the locations of the viral families in density-size space could be mapped systematically, providing a look-up table that would be useful for distinguishing between viral and non-viral material.

FIG. 4 shows data for a similar analysis on a known sample, prepared of MS2 bacteriophage of known concentration, $10^{12}$ pfu/ml. After ultrafiltering 0.5 ml of the known sample as described above for the blind samples, without prefiltering, a 50 microliter sample was analyzed with the ES-DMA-CNC combination. FIG. 4 shows that the virus was easily detected, and the virions are counted and sized. The size obtained from the DMA was 26 nm, in agreement with literature for scanning electron microscopy (SEM) analysis on Leviviridae. The linewidth (full-width at half-max, or FWHM) was small at only 2 nm, indicating that the size can be determined very accurately and that viruses of a single type can be distinguished from other viruses and non-viral particles with high reliability.

In addition, the ultrafiltered known sample in FIG. 4 was diluted successively by factors of 2, down to a dilution of 128, and analyzed in the ES-DMA-CNC. Even at 1/128, the peak was still easily distinguished, giving a signal-to-noise ratio of approximately 10:1. FIG. 5, shows the peak amplitudes and areas which are plotted as a function of dilution (relative sample concentration, with the undiluted sample having a value of unity). FIG. 5 demonstrates the linearity of the detection method.

FIG. 8 discloses one embodiment of an arrangement 110 of utilizing concentration, purification and detection devices for detecting the presence of virus particles. The detection apparatus 110 includes an input control section 111 for receiving a test sample through inlet 112 and two gas-phase electrophoretic mobility molecular analyzers (GEMMA) 126 and 156, each of which comprises the electrospray (ES), the differential mobility analyzer (DMA), and the condensation particle counter (CPC) assembly, as described above. The arrangement of FIG. 8 also includes ultrafilter modules 114 and 135 which are selectively used with the GEMMAs 126 and 156 for detecting the presence of virus particles in various types of samples. In a first configuration, the apparatus can be configured to process a "dirty sample", which is defined as a sample containing a known virus of along with other impurities, such as growth media, salts and proteins. The dirty sample is fed through conduit or tube 113 to a first ultra-filtration(UF) module 114, as shown in FIGS. 9 and 10, where the sample is further concentrated. The first ultrafiltration(UF) module 114 could utilize a cross-flow type of ultrafilter 116, as depicted in cross-section in FIG. 10, where the smaller size or smaller molecular weight particles flow outwardly through the walls of the filter 116 while the larger virus particles are retained therein. Sequential arrangements of different pore size ultrafilters can be picked to selectively control the flow of a particle with a chosen size range so that the chosen particles can flow through the walls of a first filter, such as a cross flow filter, and then not pass through the walls of second filter to thereby purify and concentrate a fluid sample limited to particles within the chosen size range. The sample retained within the filter is then fed to the GEMMA unit 126 to determine the concentration of the virus particles. If the test results from the GEMMA unit 126 suggest that the concentration of the virus is too dilute, then the sample can be fed to a second ultra-filtration (UF) module 135, where the sample can be further purified and concentrated. When desired, an ultracentrifuge 108 can be selectively coupled either to the input control section 111 or an ultrafiltration module 114 after the samples have been separated into gradient density bands.

A second configuration is shown in FIG. 8 where the apparatus is configured to process a "clean sample", which is defined as a sample containing a known virus with few impurities so that the sample can be fed directly to a GEMMA unit 126. If the results from the GEMMA unit 126 suggest that the sample is too dilute, then the sample can be further concentrated by feeding the sample through conduit 129 to the second ultra-filtration module 135. To coordinate and calibrate the results from the GEMMAS, a test or tracer solution 145 of known concentration, such as MS2 bacteriophage, can be introduced into the conduits 113, 125, and 131, as represented by item number 160, so that the concentrations results indicated by the GEMMA's can be compared and calibrated. Where a known virus "test" sample is used, the test or calibration sample can be fed through conduit 125 directly to the first GEMMA unit 126. If the test results do not show the presence of the particular known virus, then the sample is then further concentrated in the second ultra-filtration module 135.

Figure 8:
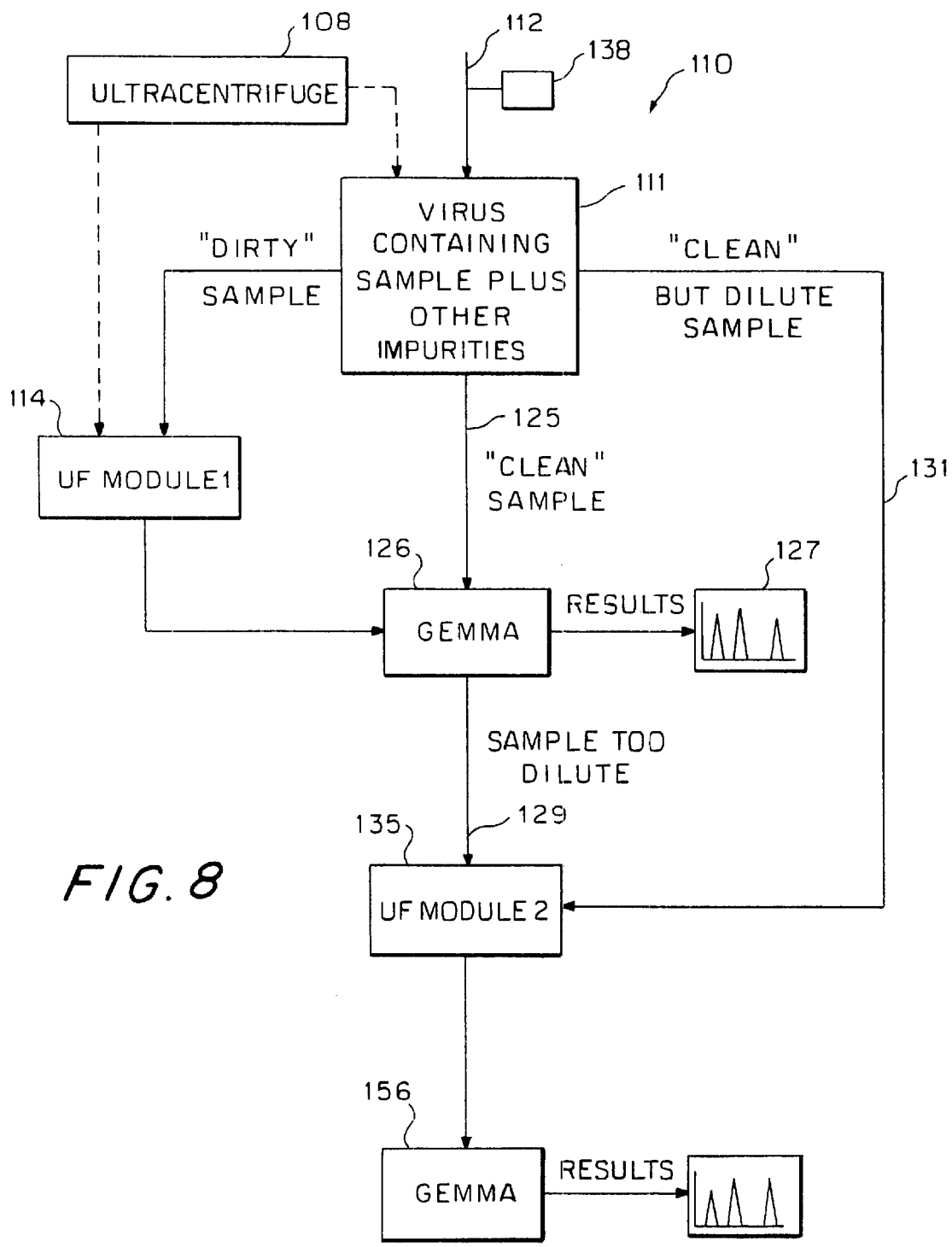
FIG. 8 is an embodiment of a concentration and detection apparatus.

A third configuration is also shown in FIG. 8 where a sample is "clean" but may be of dilute concentration. For this configuration, the sample is fed directly to the second ultrafiltration module 135 for further concentration. The concentrated sample is then fed to a second GEMMA unit 156.

Figure 9:
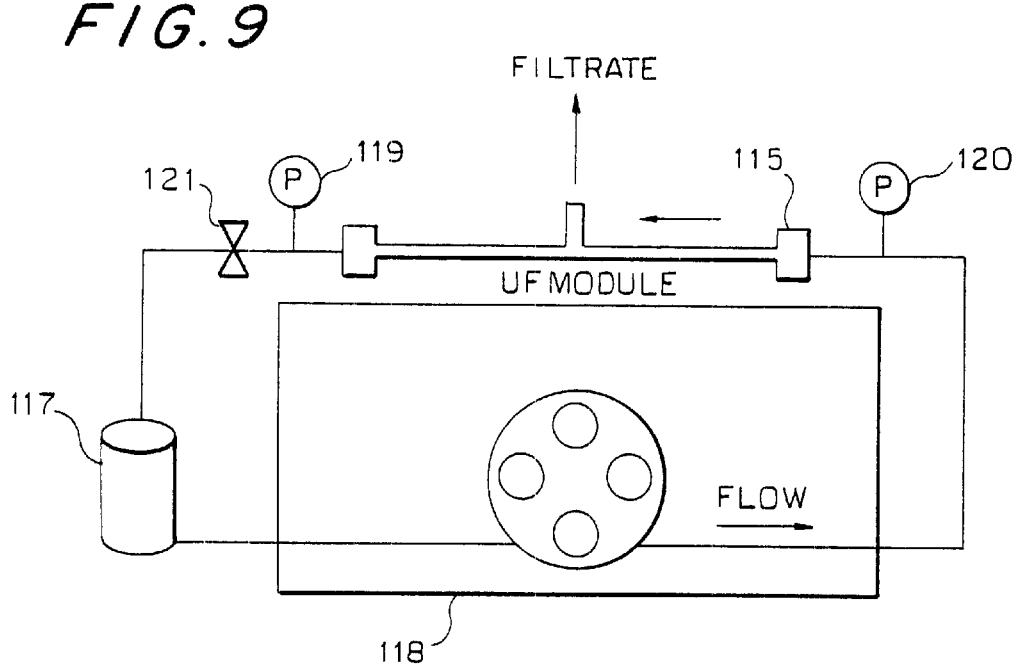
FIG. 9 is a first ultrafiltration module.
Figure 10:
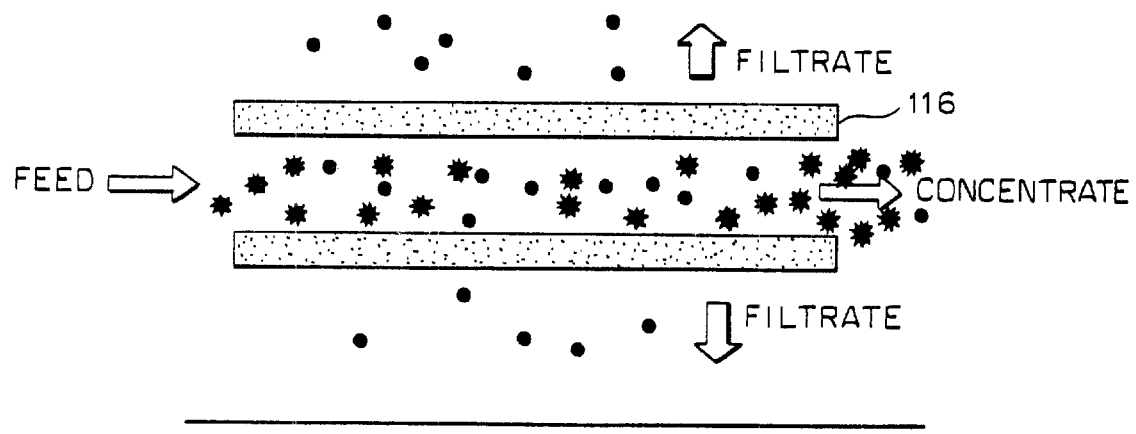
FIG. 10 is a cross-sectional representation of a filter element.

With an ultrafiltration module 114, such as generally depicted in FIG. 9, a sample is first placed in the feed reservoir 117 and then the peristaltic pump 118 is turned on to cause the sample to flow through the filter container 115. As the sample is fed through the tubular or cross-flow filter 116 housed within the filter container, the filtrate, which may include salts and proteins, is forced through the filter 116 leaving the viruses in the sample contained within the filter, as represented in FIG. 10. The speed and pressure of the peristaltic pump 118 and the settings of the inlet-outlet valve 121 can be adjusted to control the internal pressure within the system, as monitored by the pressure gauges 119 and 120. A first ultra-filtration module can be used, for example, to reduce the sample volume from about 5 milliliters to about 500 micro-liters.

Figure 11:
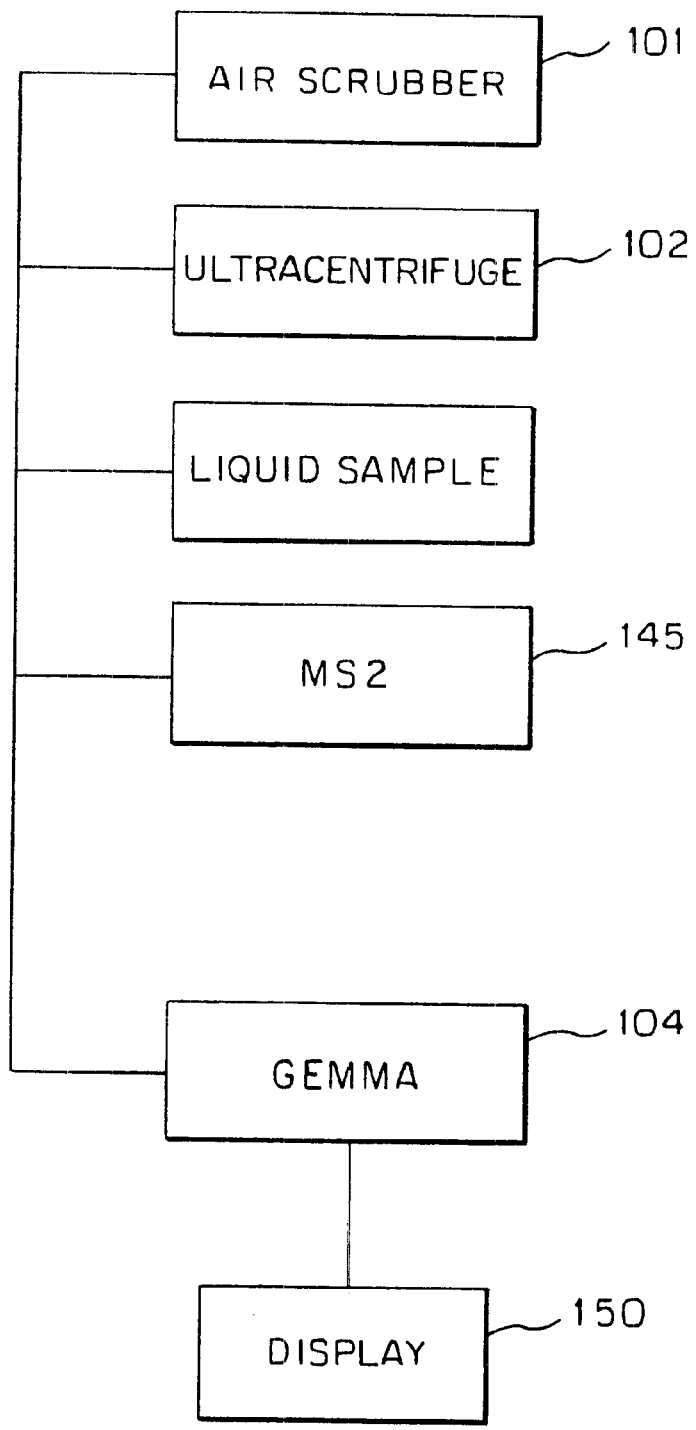
FIG. 11 is an embodiment of a particle detection system.

FIG. 11 is a schematic of FIG. 8 illustrating that a collected liquid sample having known or suspected virus or virus-like particles can be fed directly from a collection means, such as collector 1 and/or holding tank 6, ultracentrifuge extraction stage 102, or other liquid collector, to a GEMMA unit 104. This arrangement would be efficient for "clean" liquid samples and where a known material has varying concentration levels. It is further contemplated that a tracer material of known concentration, such as MS2 bacteriophage, could be introduced into the liquid sample to correlate or calibrate the outputs from the GEMMA. This would allow the use of a computer means, generally indicated as 150, that is connected to the GEMMA output for displaying the test results.

A. Tests in Removing Complex Media from MS2 Bacteriophage Cultures

A. 1 Background

To demonstrate the applicability of the apparatus for detecting viruses in samples, tests were made for removing complex growth media and other impurities, such as salts, proteins and other material, from the MS2 bacteriophage. The MS2 bacteriophage simulates the size characteristics of viruses.

A sample of MS2 bacteriophage was received from the Life Sciences Division at Dugway Proving Ground (DPG). This sample was 500 ml of as grown MS2 bacteriophage, complete with growth media, at a virus concentration of $1.4 \times 10^{12}$ pfu/ml. The growth media was comprised of L-B broth, 10 g Tryptone, 10 parts NaCl and 5 parts yeast extract. The MS2 solution was a dark yellow color and is clear. The sample was from Lot #98251.

The MS2 sample was analyzed using the ultra-filtration modules and the Gas-phase Electrophoretic Mobility Molecular Analyzer (GEMMA) detector. As noted above, the GEMMA detector consists of an electrospray unit to inject samples into the detector, a differential mobility analyzer and a condensate particle counter.

Several solutions were prepared to explore the ability of the ultrafiltration apparatus to remove contaminates and retain viruses of interest in solution. One sample solution of albumin, from chicken egg, was prepared at a concentration of 0.02%, by weight, in an ammonium acetate (0.02M) buffer. To this solution was added MS2 bacteriophage to a concentration of $3 \times 10^{11}$ pfu/ml. Another was prepared containing 2.5% cesium chloride (CsCl), by weight, also in the ammonium acetate buffer. To this solution was added MS2 bacteriophage to a concentration of $5 \times 10^{11}$ pfu/ml. The MS2 bacteriophage, in both cases, was a highly purified sample obtained from DPG Life Sciences Division (Lot #98251).

A. 2. Results of MS2 plus Growth Media

Figure 12:
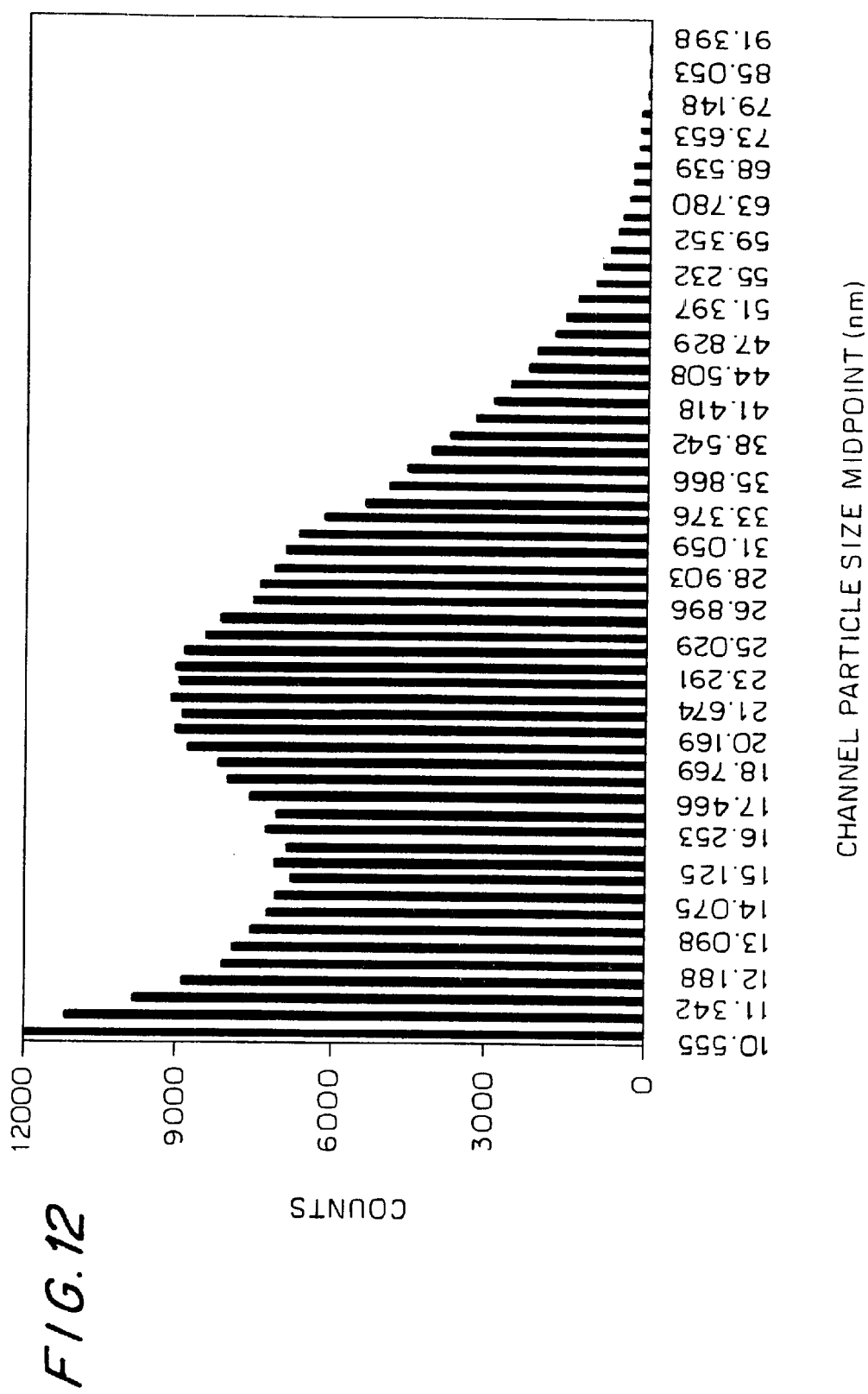
FIG. 12 is a graph of MS2 Bacteriophage with growth media.

The mixed MS2 sample, with $1.4 \times 10^{12}$ pfu/ml was analyzed using the GEMMA virus detector. The sample was placed neat into the GEMMA analyzer and the results are shown in FIG. 12. The growth media, with the MS2 bacteriophage in solution, produces a graph that displays a very broad, nondescript peak across the area of interest of 24–26 nm. The size range of 24–26 nm is the expected size for a MS2 bacteriophage. It is not readily apparent from the as received sample analysis if the sample actually contains MS2 in solution. The solution required removal of the growth media before any meaningful results could be obtained.

The virus plus growth media sample was purified and concentrated using an ultrafiltration (UF) process. The UF module, shown in FIGS. 9 and 10 were used for processing and retaining a virus species for further study. The UF stage is a hollow fiber-based tangential or cross flow filtration system. These filtration systems operate by pumping the feed stream through the hollow fiber, as shown in FIGS. 9 and 10. As the solution passes through the fiber, the sweeping action of the flow helps to prevent clogging of the fiber. A pressure differential forces the filtrate through the fiber, while the virus feed stream is purified and concentrated. There are available a wide range of pore sizes for the fibers. This filtration technique can reduce volumes from over 5 ml to about 0.2 ml.

The sample of the DPG MS2 with growth media was processed through the ultrafiltration apparatus using the parameters for ultrafiltration listed in Table 1.

TABLE 1

| UF Parameters for MS2 in Growth Media | |
| --- | --- |
| Sample volume-initial | 3 ml |
| Pump speed | 2 |
| Transducer pressure | 15 psig |
| Total buffer wash volume | 50 ml |
| Sample volume-final | 2 ml |
| MWCO of module | 500K |

Figure 13:
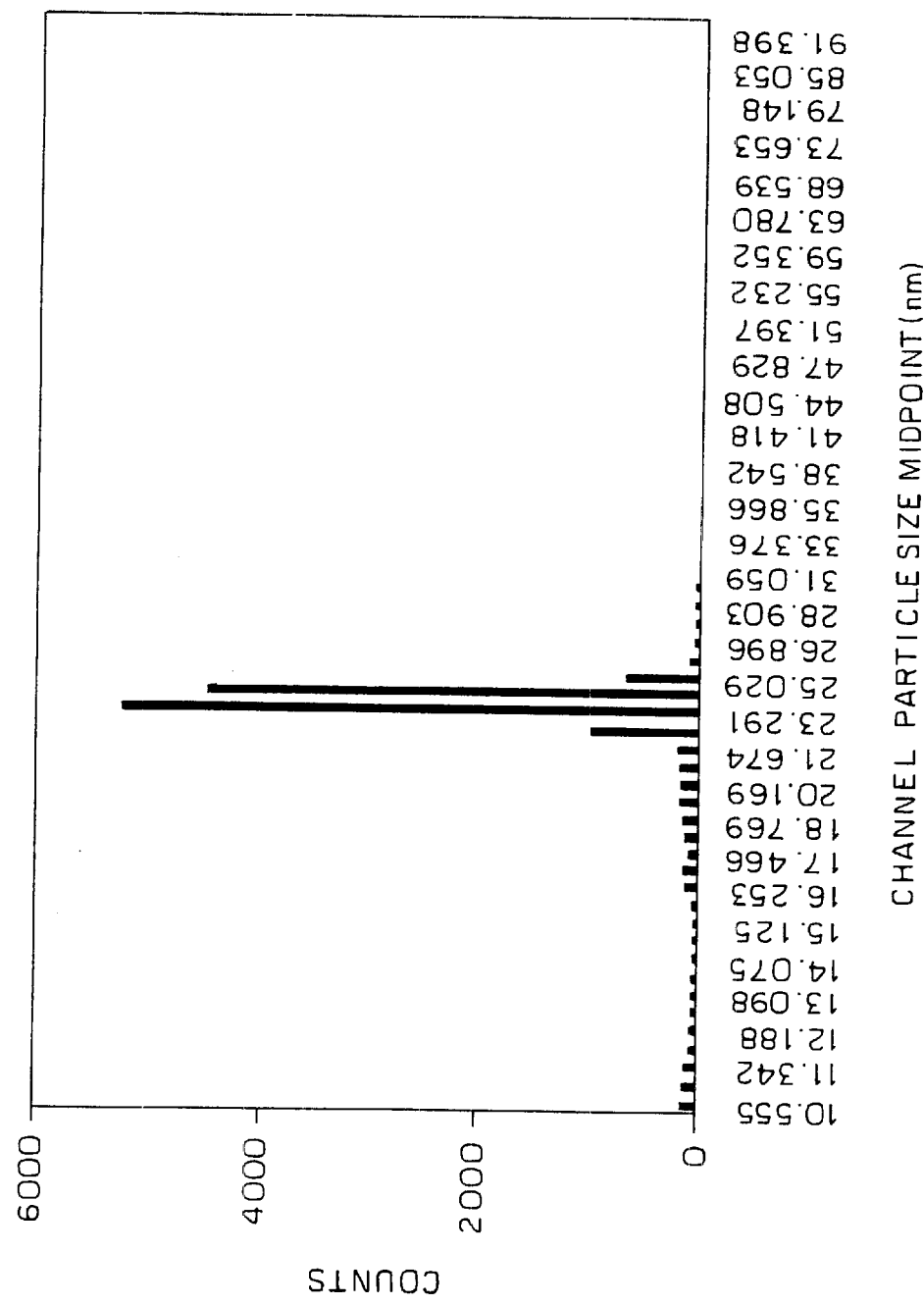
FIG. 13 are results of the MS2 Bacteriophage with growth media after ultrafiltration.

By continually washing the sample volume with ammonium acetate buffer (the working fluid of the GEMMA analyzer), the UF apparatus allows the removal of ions, proteins and all other material that is smaller than the 500K molecular weight cut-off (MWCO) of the cross flow filter. The MS2 bacteriophage is retained in the circulating solution and continued to be purified by the process. As the 500K MWCO filter will effectively retain the MS2, the total wash volume can be significantly larger than the initial sample volume. The ultrafiltration of this sample was completed in less than 10 minutes. The results of the GEMMA analysis of the concentrated and purified sample are shown Table 2, below, and in FIG. 13.

Table 2

GEMMA Counts for MS2 Bacteriophage

| Channel Midpoint Diameter (nm) | Counts |
| --- | --- |
| 10.5545 | 128.2 |
| 10.9411 | 105.7 |
| 11.3419 | 97.7 |
| 11.7574 | 64.3 |
| 12.1881 | 37.3 |
| 12.6346 | 50.8 |
| 13.0975 | 34.2 |
| 13.5773 | 36.8 |
| 14.0746 | 39.5 |
| 14.5902 | 34.6 |
| 15.1247 | 28 |
| 15.6788 | 41.5 |
| 16.2531 | 102.1 |
| 16.8485 | 110.8 |
| 17.4658 | 80.3 |
| 18.1056 | 120.7 |
| 18.7688 | 129.4 |
| 19.4564 | 167 |
| 20.1691 | 175.2 |
| 20.908 | 168.6 |
| 21.6739 | 192.2 |
| 22.4679 | 973.1 |
| 23.291 | 5228.2 |
| 24.1442 | 4429.7 |
| 25.0287 | 639.9 |
| 25.9455 | 73.6 |
| 26.896 | 31.4 |
| 27.8813 | 25.6 |
| 28.9026 | 22 |
| 29.9614 | 195 |
| 31.059 | 16.2 |
| 32.1968 | 17.5 |
| 33.3762 | 8.5 |
| 34.5989 | 10.5 |
| 35.8664 | 7.5 |
| 37.1803 | 6.5 |
| 38.5423 | 2.5 |
| 39.9542 | 3 |
| 41.4178 | 6.8 |
| 42.9351 | 2.2 |
| 44.5079 | 5 |
| 46.1384 | 2 |
| 47.8286 | 1 |
| 49.5807 | 2 |
| 51.397 | 1 |
| 53.2798 | 0 |
| 55.2316 | 1 |
| 57.2549 | 0 |
| 59.3523 | 0 |
| 61.5265 | 1 |
| 63.7804 | 1 |
| 66.1169 | 0 |
| 68.539 | 1 |
| 71.0497 | 1 |
| 73.6525 | 1 |
| 76.3506 | 0 |
| 79.1476 | 1 |
| 82.047 | 0 |
| 85.0526 | 0 |
| 88.1683 | 2 |
| 91.3982 | 0 |

A. 3. Results of MS2 plus Albumin

Figure 14:
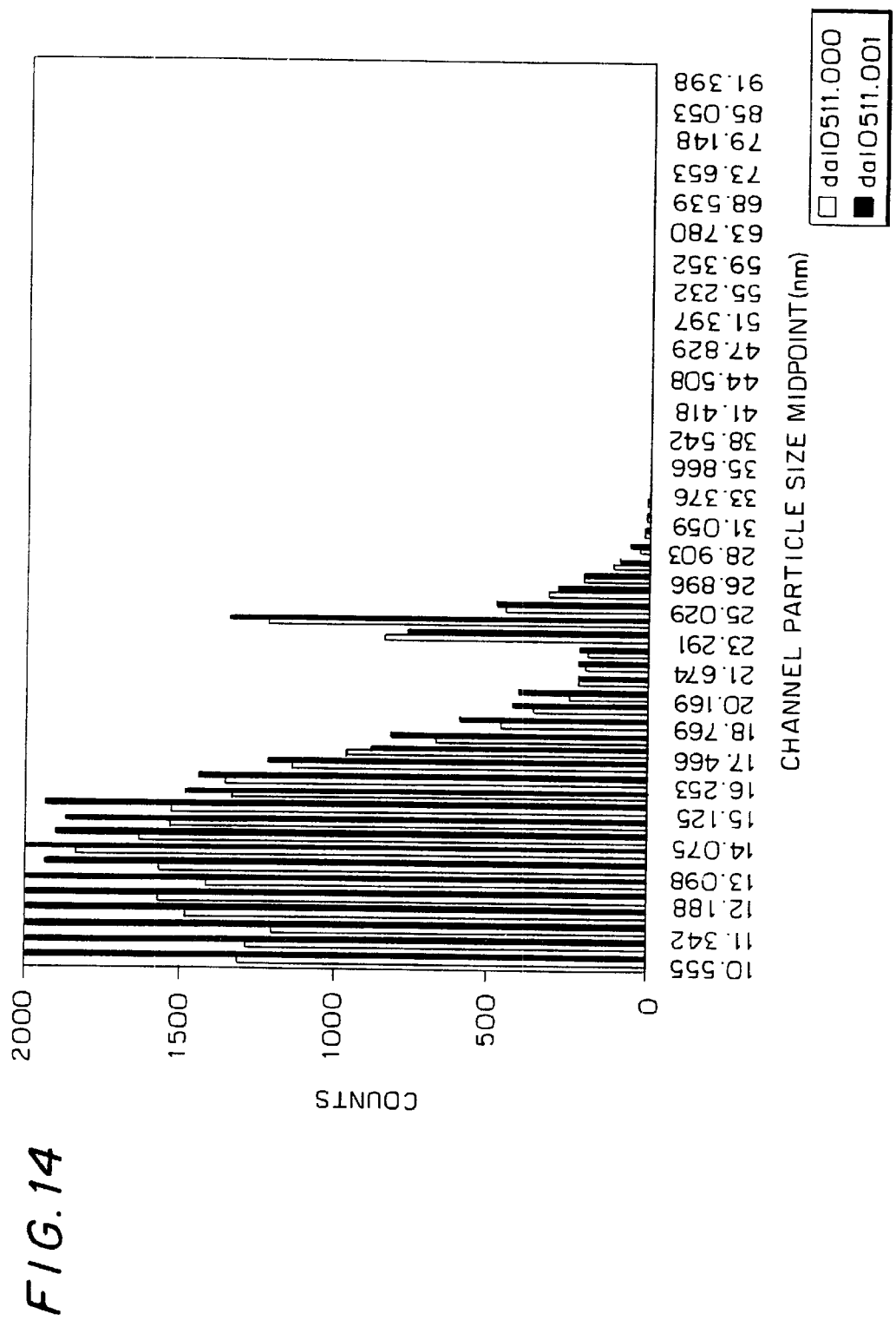
FIG. 14 is a graph of MS2 Bacteriophage with albumin.

The sample of 0.02% albumin in ammonium acetate, with the addition of 3×1011 pfu/ml of MS2 bacteriophage, was analyzed neat in the GEMMA virus detector. The MS2 peak is centered around 24 nm. The albumin in the sample is displayed as a very broad peak starting below 10 nm and extending to 20 nm, as shown in FIG. 14.

The sample of albumin plus MS2 was then processed through the ultrafiltration apparatus. The parameters for the ultrafiltration are shown in Table 3.

TABLE 3

UF Parameters for Albumin plus MS2

| | |
| --- | --- |
| Sample volume-initial | 1 ml |
| Pump speed | 2 |
| Transducer pressure | 15 psig |
| Total buffer wash volume | 40 ml |
| Sample volume-final | 0.4 ml |
| MWCO of module | 500K |

Figure 15:
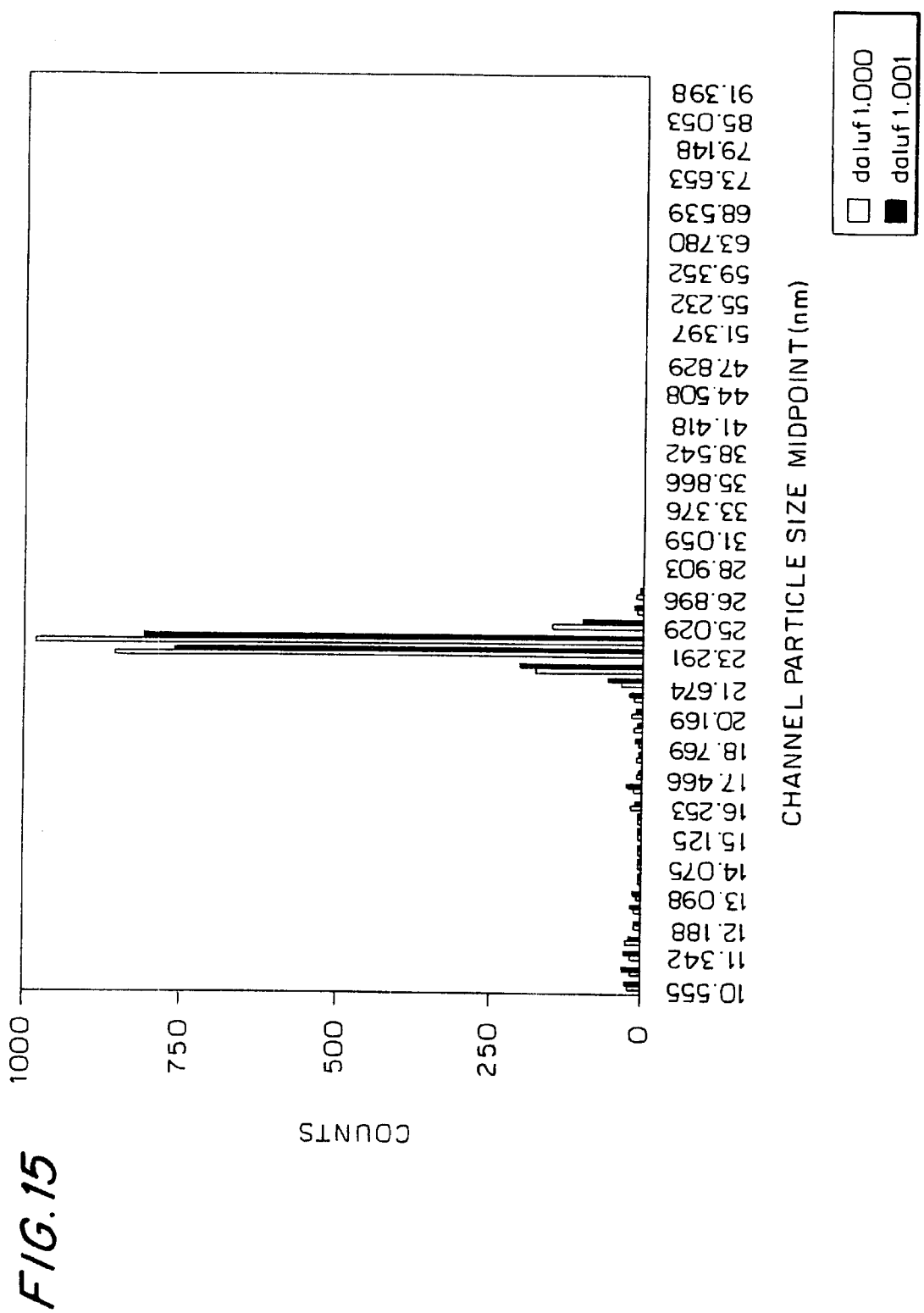
FIG. 15 are results of MS2 Bacteriophage with albumin after ultrafiltration.

After processing in the ultrafiltration apparatus, the sample was examined in the GEMMA virus detector. As shown in FIG. 15, the only peak in evidence is centered on 24 nm. The large peak between 10 and 20 nm was completely removed. The processing of the sample through the ultrafiltration apparatus completely removed the albumin protein, while the MS2 bacteriophage was retained.

A. 4. Results of MS2 plus Cesium Chloride

Figure 16:
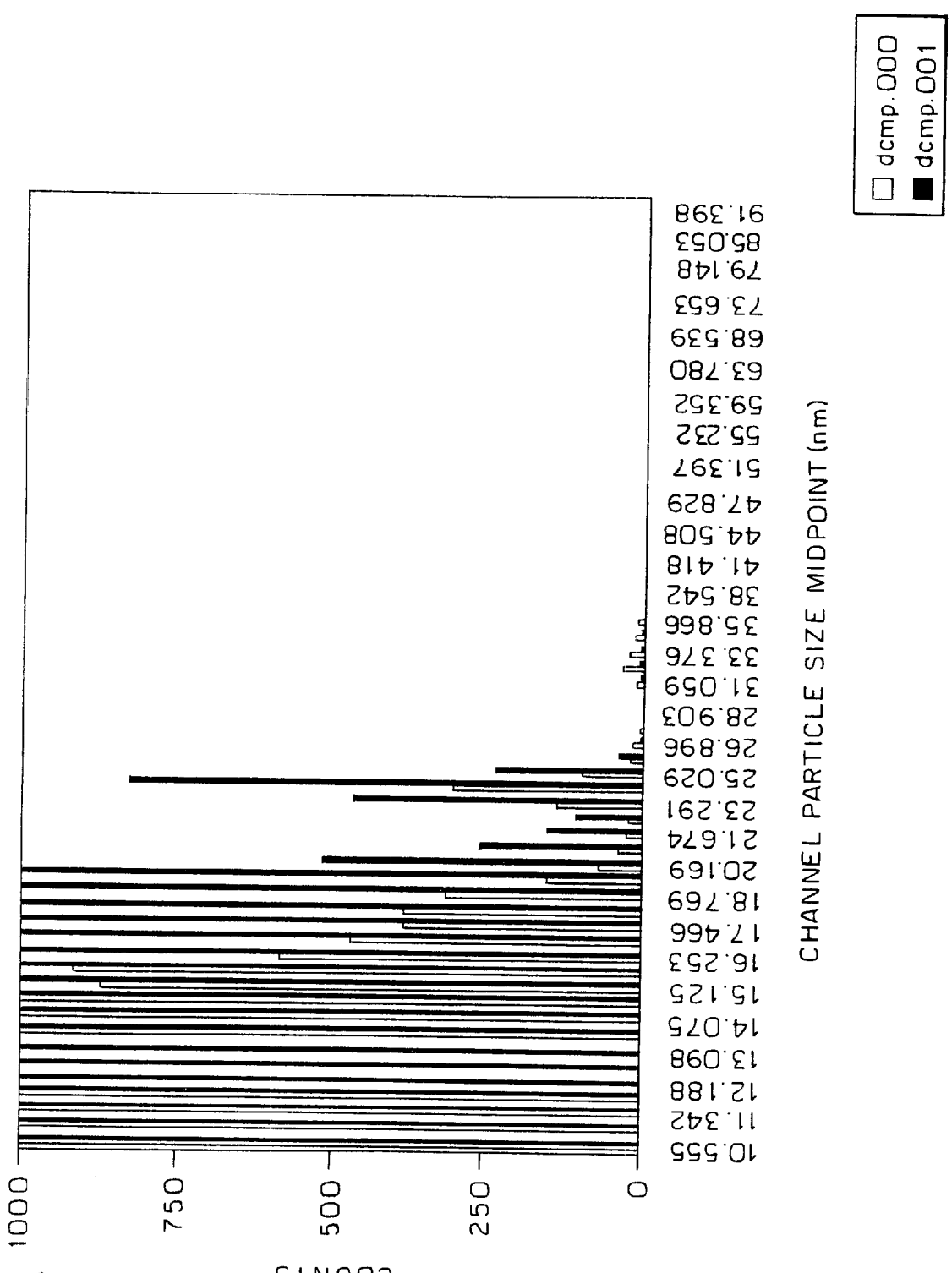
FIG. 16 is a graph of MS2 Bacteriophage with cesium chloride.

The sample of 2.5% CsCl, by weight, in ammonium acetate, with the addition of 5×1011 pfu/ml of MS2 bacteriophage, was analyzed neat in the GEMMA virus detector. As shown in FIG. 16, the MS2 peak is centered around 24 nm. The CsCl in the sample is displayed as a very broad peak starting below 10 nm and extending to over 20 nm. Any higher concentrations of CsCl would start to obscure the MS2 peak position.

The sample of CsCl plus MS2 was then processed through the ultrafiltration apparatus. The parameters for the ultrafiltration are shown in Table 4.

TABLE 4

UF Parameters for CsCl plus MS2

| | |
| --- | --- |
| Sample volume-initial | 1 ml |
| Pump speed | 2 |
| Transducer pressure | 15 psig |
| Total buffer wash volume | 30 ml |
| Sample volume-final | 0.5 ml |
| MWCO of module | 500K |

Figure 17:
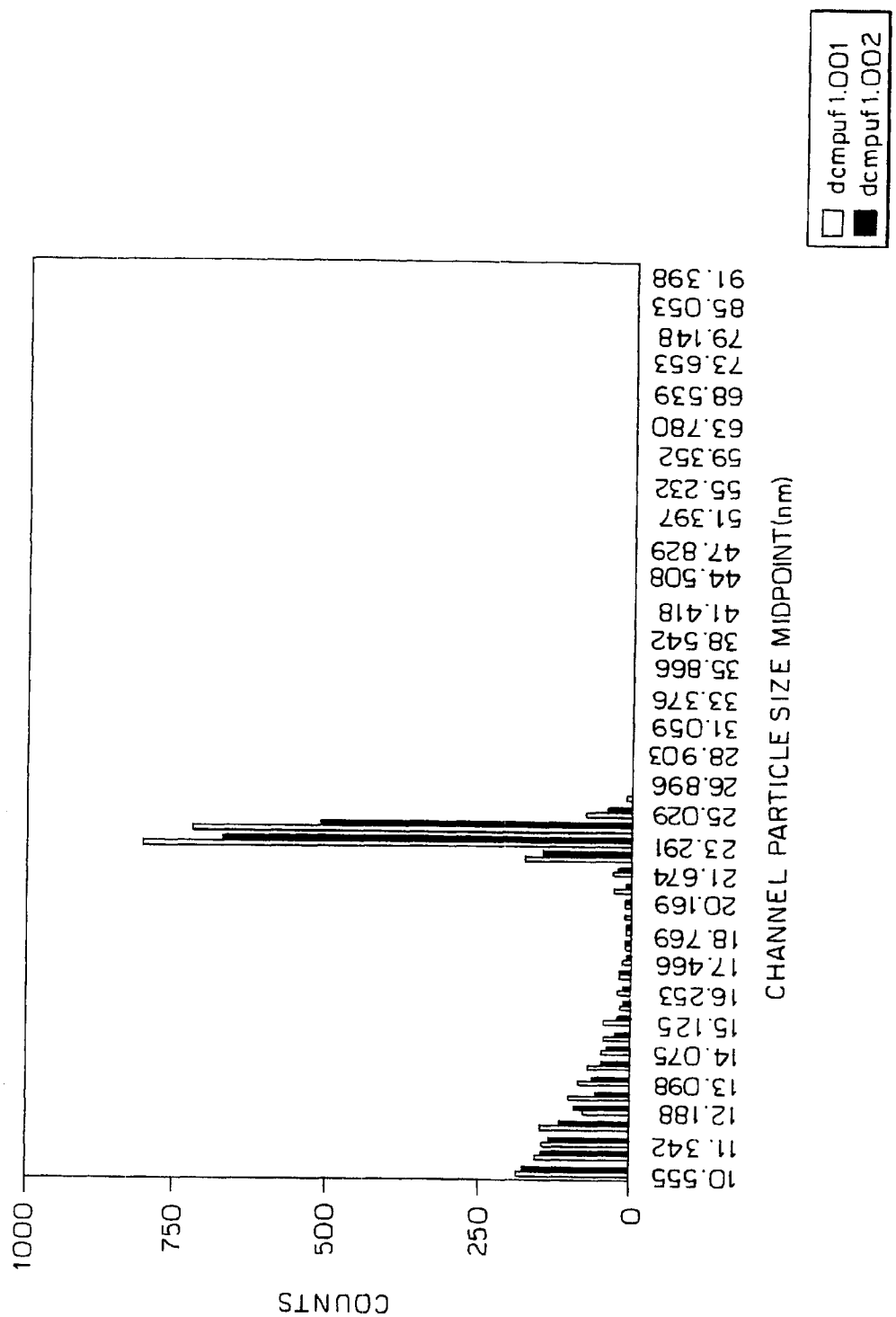
FIG. 17 are results of MS2 Bacteriophage with cesium chloride after ultrafiltration.

After processing in the ultrafiltration apparatus, the sample was examined in the GEMMA virus detector. As shown in FIG. 17, the MS2 peak is shown centered on 24 nm. The large peak between 10 and 22 nm was significantly removed. There was a small remnant of the CsCl peak in the processed sample due to the smaller amount of buffer wash volume in this cycle. To completely remove the CsCl, the ultrafiltration process would only need to be continued with further washing until all of the salt was replaced with buffer solution. The processing of this sample through the ultrafiltration apparatus also retained the MS2 bacteriophage.

A. 5. Analysis

The ultrafiltration apparatus was very effective in removing the growth media from the solution of MS2 bacteriophage. The addition of approximately ten times the amount of starting solution with ammonium acetate buffer (3 ml vs. 50 ml respectively) allowed the efficient replacement of the growth media with the buffer solution. The background of the GEMMA scan of the ultrafiltration-processed solution was very low due to the low detection of ammonium acetate. In addition, the ultrafiltration process for comparable volumes can be completed in approximately 10 minutes.

The addition of other contaminating materials in a virus solution can also be successfully removed from solution while retaining the virus. The albumin protein was almost completely removed from the MS2 containing solution by ultrafiltration. The adjustment (if necessary) of the pore size of the ultrafiltration modules allows for great flexibility in the processing of solutions.

The CsCl solution appeared to require further washing to completely remove the salt from the virus containing solution. From the tests to date, it appears that the wash volume for the removal of CsCl in the ultrafiltration apparatus requires the initial sample volume to be washed with approximately 40–50 times the volume of buffer solution, for certain impurities, to completely remove those impurities.

B. Tests of Effective Filter Size in Concentrating MS2 Bacteriophages

Nominal molecular weight cut off values (MWCO) of various filters has often lead to the assumption that items larger than the cut off values will be retained after filtration. It was discovered that, at least for MS2 bacteriophage, there are exceptions. It was discovered during the filtration operation, that counts of MS2 decreased during repeated cycles of ultrafiltration and purification. This was an important discovery in that for the detection of small numbers of viruses, any loss may be important. As a result, this study was initiated to better understand the cross-flow filtration characteristics of MS2 bacteriophage. The sample of MS2 bacteriophage, used in the filtration studies, was received from the Life Sciences Division at Dugway Proving Ground (DPG). This sample was 2 ml of purified MS2 bacteriophage at a concentration $1\times10^{14}$ pfu/ml or 10.2 mg protein/ml. This highly purified sample is from Lot #98110.

The two types of filters used in this study were a centrifuge tube assembly, where the solution is forced through the filter by gravitational forces and a cross flow filter apparatus of FIGS. 9 and 10 with pressure pushing the solution through the filter. The centrifuge filter assemblies are available in various sizes and molecular weight cut off (MWCO) filter inserts. The MWCO is changed to capture biological material, such as proteins, cell products and viruses, by molecular weight differentiation. The cross flow filter, or ultrafiltration apparatus, is also used to capture or reject biological material by adjusting the MWCO of the filter. These filtration systems operate by pumping the feed stream through a hollow fiber. As the solution passes through the fiber, the sweeping action of the flow helps to prevent clogging of the fiber. A pressure differential forces the filtrate through the fiber, while the biological feed stream is purified and concentrated. There are available a wide range of pore sizes for the centrifuge filters as well as the hollow fiber filters.

The MS2 samples were analyzed after filtration using the GEMMA detector, consisting of an Electrospray unit to inject samples into the detector, a Differential Mobility Analyzer and a Condensate Particle Counter.

B.1. Test Solutions

The first set of solutions consisted of $1\times10^{11}$ pfu/ml of MS2 in a cesium chloride (CsCl) solution (0.5%, by weight) in an ammonium acetate buffer (0.02M). The procedure in these cases was to place 150 µl of the solution into a wedge filter of differing molecular weight cut-off (MWCO). The MWCO used were 30K, 50K and 100K Dalton. The filter was then centrifuged and the samples were analyzed in the GEMMA. As shown in Table 5, the wedge filters all concentrated the MS2 solution, i.e. the counts increased as the solution size decreased. Even with a subsequent addition of buffer and re-centrifugation, the solutions continue to concentrate.

The same solution (CsCl 0.5%+$1\times10^{11}$ pfu/ml MS2) was then placed into a 1M Dalton centrifuge filter and spun. The first concentration shows an increase from 150 counts to 350 counts in the sample. The solution volume decreasing, from 1000 to 100 µl, should increase the counts measured. The subsequent wash and re-centrifugation should show an increase in MS2 counts. However, the counts for the washed sample are even lower. The conclusion from the filtration with the 1M MWCO filter is that the MS2 bacteriophage is able to pass through the filter and is not retained.

TABLE 5

Filtration of MS2 plus CsCl Solutions

| Sample | Filter MWCO (Daltons) | Counts | Volume (µl) | +1 Wash (counts) | Volume (µl) |
|---|---|---|---|---|---|
| CsCl 0.5% + 1x10¹¹ MS2, DPG | None | 150 | 150 | | |
| CsCl 0.5% + 1x10¹¹ MS2, DPG | 30K | 2500 | 25 | 4500 | 35 |
| CsCl 0.5% + 1x10¹¹ MS2, DPG | 50K | 2000 | 20 | 3000 | 25 |
| CsCl 0.5% + 1x10¹¹ MS2, DPG | 100K | 9000 | 15 | 5000 | 10 (+5 buffer) |
| CsCl 0.5% + 1x10¹¹ MS2, DPG | 1 M centrifuge | 350 | 100 | 75 | 50 |

Figure 18:
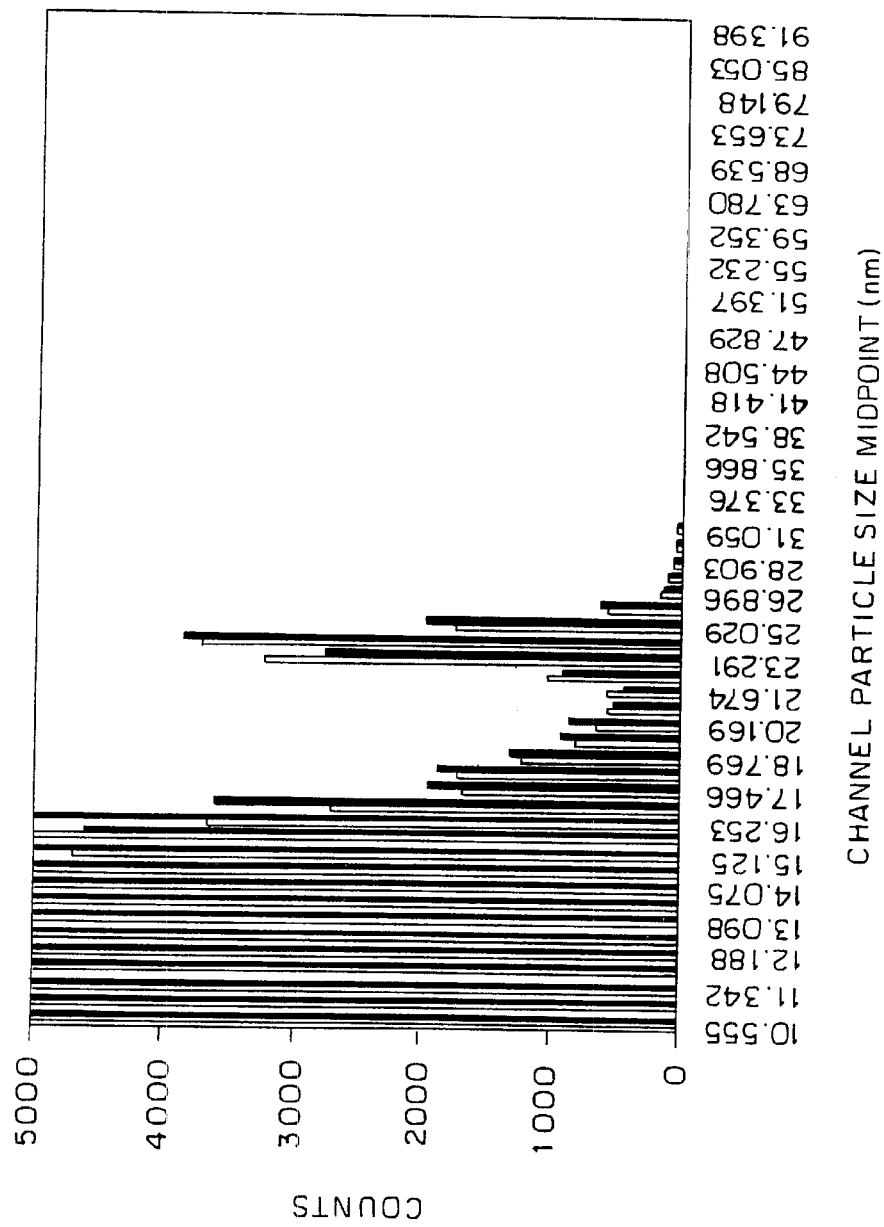
FIG. 18 are results of MS2 filtered with a 1M centrifuge filter.

To actually determine if the MS2 is passing through the centrifuge filters, the filtrate should be analyzed. A separate sample of $1\times10^{12}$ pfu/ml MS2 (DPG ultrafiltration cleaned, mixed media sample) was filtered with the 1M centrifuge filters. As shown in FIG. 18, the /MS2 passed through the filter and was deposited in the filtrate. Table 6 presents the numerical counts from the GEMMA analysis of the retentate, after one wash cycle, and the filtrate from the 1M centrifugation of the sample.

TABLE 6

Filtration of MS2 Solution after Ultrafiltration Processing

| Sample | Filter MWCO (Daltons) | GEMMA Counts | Volume (µl) | +1 Wash (counts) | Volume (µl) |
|---|---|---|---|---|---|
| DPG MS2 Mixed Media UF Mod 1 | none | 5000 | 100 | | |
| DPG MS2 Mixed Media UF Mod 1 Retentate | 1 M centrifuge | | | 75 | 100 |
| DPG MS2 Mixed Media UF Mod 1 Filtrate | 1 M centrifuge | 3,500 | 150 | | |

To determine if there was any interference from the CsCl during the filtration with the 1M filters, a solution of MS2 was prepared at a concentration of $1\times10^{11}$ pfu/ml by dilution in the ammonium acetate buffer only. The sample was prepared from a stock solution obtained from the Life Sciences Division of Dugway Proving Ground (DPG). The MS2 solution was then centrifuged in the 1M centrifuge filter. As shown in Table 7, the plain MS2 solution also passed through the 1M filter apparatus with the loss of virus material. The CsCl does not appear to affect the loss of virus material by its presence in the filtration solution.

TABLE 7

Filtration of Pure MS2 Solutions

| Sample | Filter MWCO (Daltons) | GEMMA Counts | Volume (μl) |
|---|---|---|---|
| 1x1011 MS2, DPG | None | 600 | 100 |
| 1x1011 MS2, DPG Retentate | 1 M centrifuge | 65 | 100 |

Another type of filtration is the cross flow or tangential flow technique. The solution is pumped through a hollow fiber that is designed to allow the passage of differing MWCO materials, depending on the filter installed. A flow restriction at the exit from the fiber bundle develops a pressure differential that forces the filtrate through the fiber and concentrates the feed solution, as shown in FIGS. 9 and 10.

The first sample prepared for filtration was a CsCl (0.05%, by weight) solution with 3×1011 pfu/ml MS2 added into the ammonium acetate buffer. The ultrafiltration parameters for this solution are shown in Table 8. As shown in Table 9, the sample volume was concentrated from 1000 to 100 μl, but the counts dropped from 3200 to 25. This drop in counts shows that the cross flow filter, at a MWCO of 750K Dalton, is allowing the virus to pass through the hollow fiber.

TABLE 8

Cross Flow Parameters for CsCl (0.05%) plus MS2 (3x1011)

| | |
|---|---|
| Sample volume-initial | 1 ml |
| Pump speed | 2 |
| Transducer pressure | 15 psig |
| Total buffer wash volume | 40 ml |
| Sample volume-final | 0.1 ml |
| MWCO of module | 750K |

TABLE 9

Cross Flow Filtration of CsCl (0.05%) plus MS2 (3x1011)

| Sample | Filter MWCO (Daltons) | GEMMA Counts | Volume (μl) |
|---|---|---|---|
| CsCl 0.05% + 3x1011 MS2, DPG | None | 3200 | 1000 |
| CsCl 0.05% + 3x1011 MS2, DPG Retentate | UF Mod1 750K | 25 | 100 |

The second sample tested, a CsCl solution (2.5%, by weight) plus 5×1011 pfu/ml MS2 in ammonium acetate buffer, was processed through the cross flow filtration apparatus with a filter of 500K MWCO. The parameters for the ultrafiltration processing of the solution are shown in Table 10. Although the sample volume was concentrated by half, the counts remained constant, as shown in Table 11. It appears that the MS2 virus is also passing through the 500K filter, although at a slower rate than the 750K filter.

TABLE 10

Cross Flow Parameters for CsCl (2.5%) plus MS2 (5x1011)

| | |
|---|---|
| Sample volume-initial | 1 ml |
| Pump speed | 2 |

TABLE 10-continued

Cross Flow Parameters for CsCl (2.5%) plus MS2 (5x1011)

| | |
|---|---|
| Transducer pressure | 15 psig |
| Total buffer wash volume | 30 ml |
| Sample volume-final | 0.5 ml |
| MWCO of module | 500K |

TABLE 11

Cross Flow Filtration of CsCl (2.5%) plus MS2 (5x1011)

| Sample | Filter MWCO (Daltons) | GEMMA Counts | Volume (μl) |
|---|---|---|---|
| CsCl 2.5% + 5x1011 MS2, DPG | None | 800 | 1000 |
| CsCl 2.5% + 5x1011 MS2, DPG Retentate | UF Mod1 500K | 750 | 500 |

Figure 19:
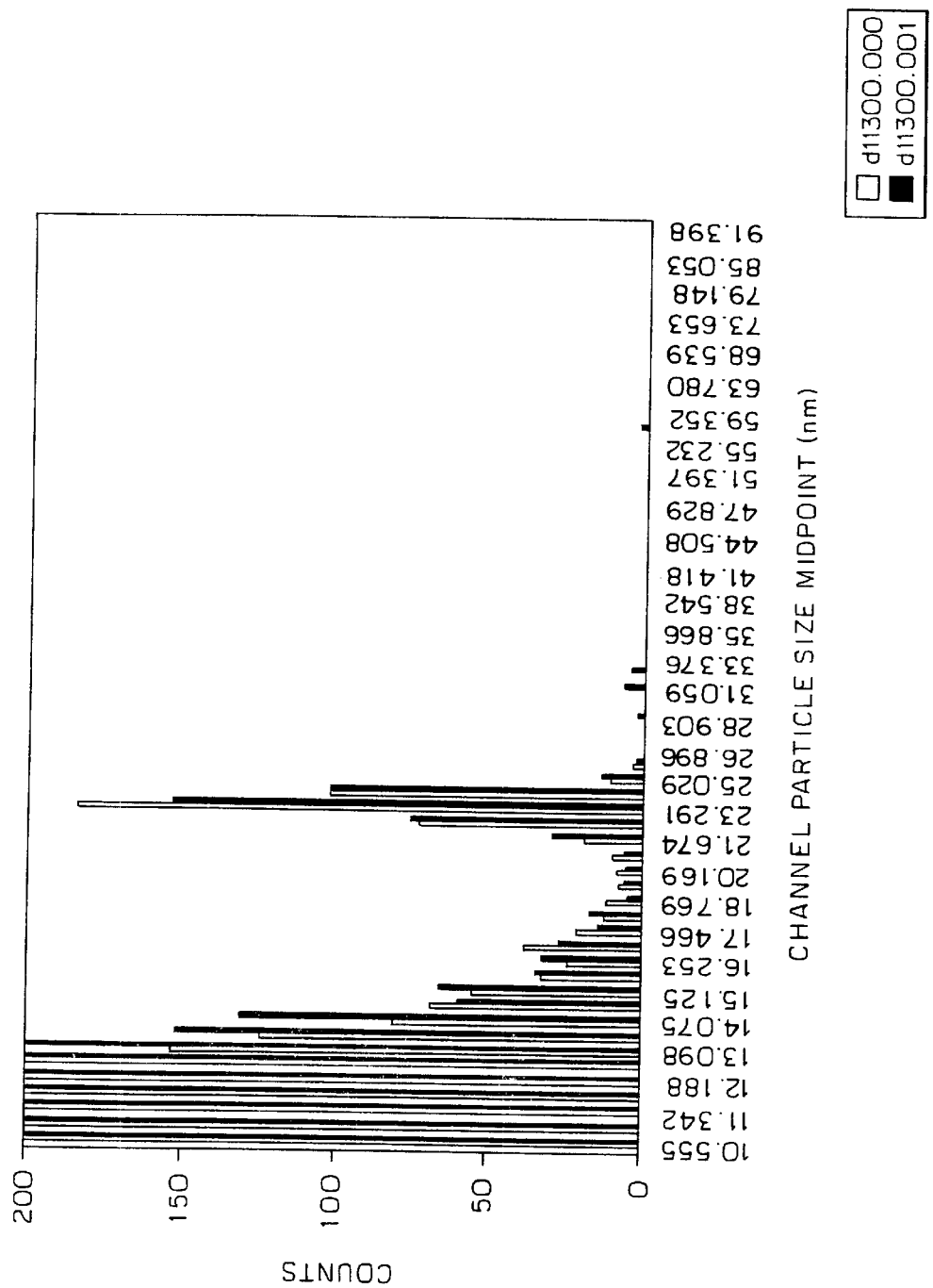
FIG. 19 are results of MS2 filtered with a 300K centrifuge filter.

To test the lower limit of MWCO for a MS2 bacteriophage, a centrifuge filter of 300K MWCO was obtained. It appears from Table 1 that the filters up to 100K MWCO do not allow the passage of MS2 through the filter medium. The 300K filter was loaded with 100 μl, diluted to 1 ml in ammonium acetate buffer, of a 1×1011 pfu/ml MS2 sample from DPG. The sample was centrifuged and the retentate analyzed. As shown in FIG. 19, the MS2 is at least partially retained in the 300K filter.

Figure 20:
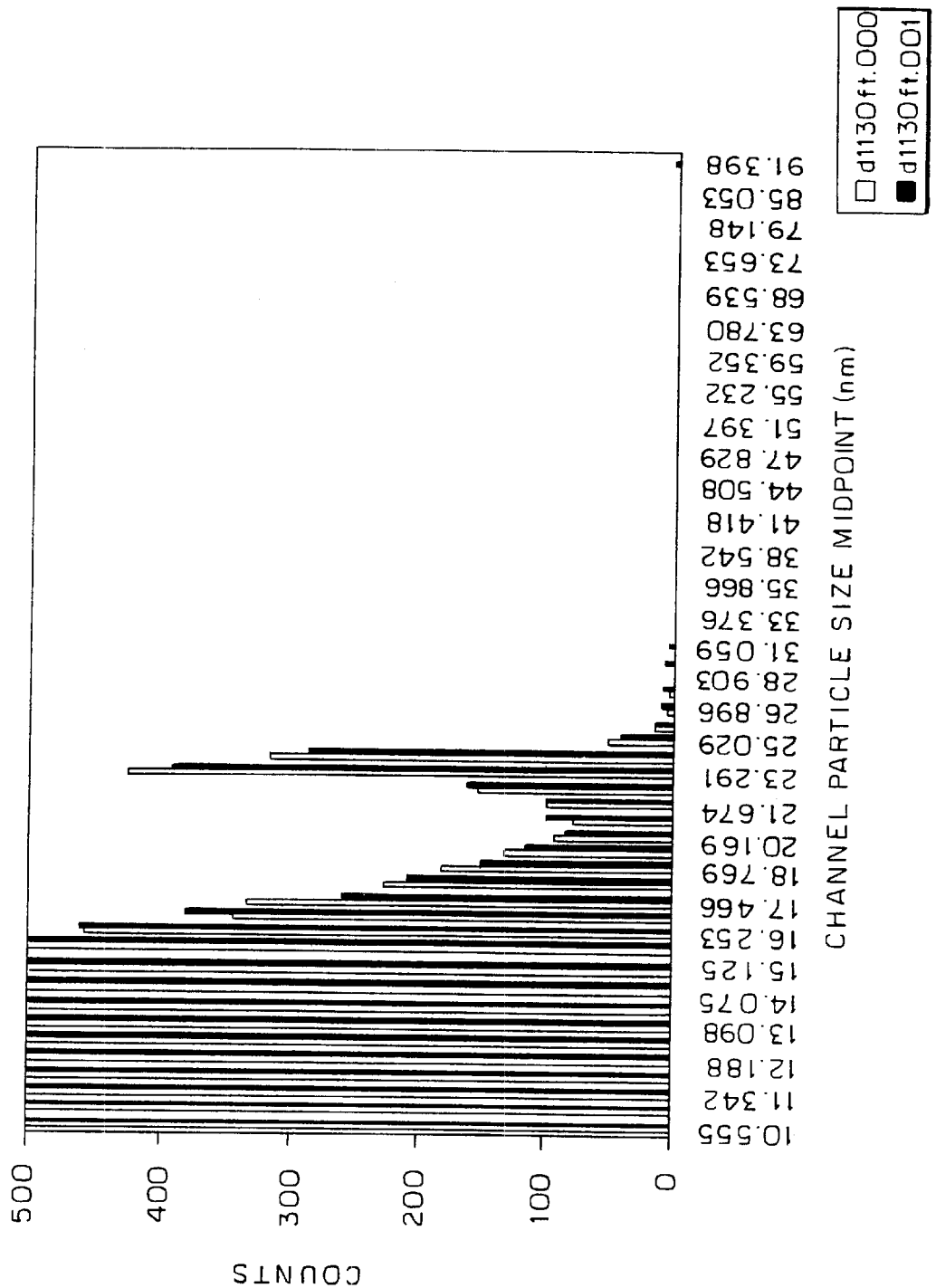
FIG. 20 are results of MS2 in the filtrate.

To determine the amount, if any, of MS2 passing through the filter, a 1 ml portion of the filtrate was concentrated in the 100K wedge filters. The final volume was reduced to 25 μl. As shown in FIG. 20, there was MS2 present in the filtrate from the 300K centrifuge filtration. It would appear that the MS2 is able to pass through MWCO filters as small as 300K. The MS2 does not appear to pass through the 100K centrifuge filters.

A series of solutions of 1×1012 pfu/ml of MS2 bacteriophage will be filtered with the cross flow apparatus with a 750K MWCO ultrafilter installed. All of the filtered solutions will include 1 ml of the 1×1012 pfu/ml MS2 with various additions of ammonium acetate buffer solution. The additions of buffer will allow differing lengths of time of filtration, in the cross flow apparatus, while keeping the amount of MS2 in the sample constant. However, the concentration of the MS2 will vary depending on the dilution factor in the starting sample. The samples will be processed in the cross flow apparatus until concentrated to approximately the 1 ml volume of the 1×1012 pfu/ml MS2 initial sample. Table 12 presents the filtration parameters for the cross flow apparatus for this set of experiments. Table 13 shows the starting volumes, initial dilution's, final sample volume and subsequent GEMMA sample count for the MS2 viral peak.

TABLE 12

Cross Flow Parameters for MS2 (1x1012) plus Variable Volume Ammonium Acetate Buffer

| | |
|---|---|
| Sample volume-initial | 1 ml MS2 + variable buffer volumes |
| Pump speed | 2 |
| Transducer pressure | 15 psig |
| Total buffer wash volume | variable |
| Sample volume-final | 0.70–0.75 ml |
| MWCO of module | 750K |

TABLE 13

Dilution Amounts and GEMMA Analysis of Cross Flow Filtration of MS2 Samples

| MS2 Start Volume | Ammonium Acetate Dilution (ml) | Final Volume (ml) | GEMMA Counts for MS2 Peak (avg. of 2 runs) |
|---|---|---|---|
| 1 ml @ 1×1012 pfu/ml | 0 | 1.0 | 9255 |
| 1 ml @ 1×1012 pfu/ml | 1 | 0.75 | 5164 |
| 1 ml @ 1×1012 pfu ml | 2 | 0.70 | 5280 |
| 1 ml @ 1×1012 pfu/ml | 4 | 0.75 | 3239 |
| 1 ml @ 1×1012 pfu/ml | 8 | 0.70 | 5284 |
| 1 ml @ 1×1012 pfu/ml | 16 | 0.75 | 3549 |
| 1 ml @ 1×1012 pfu/ml | 32 | 0.70 | 2830 |

Figure 21:
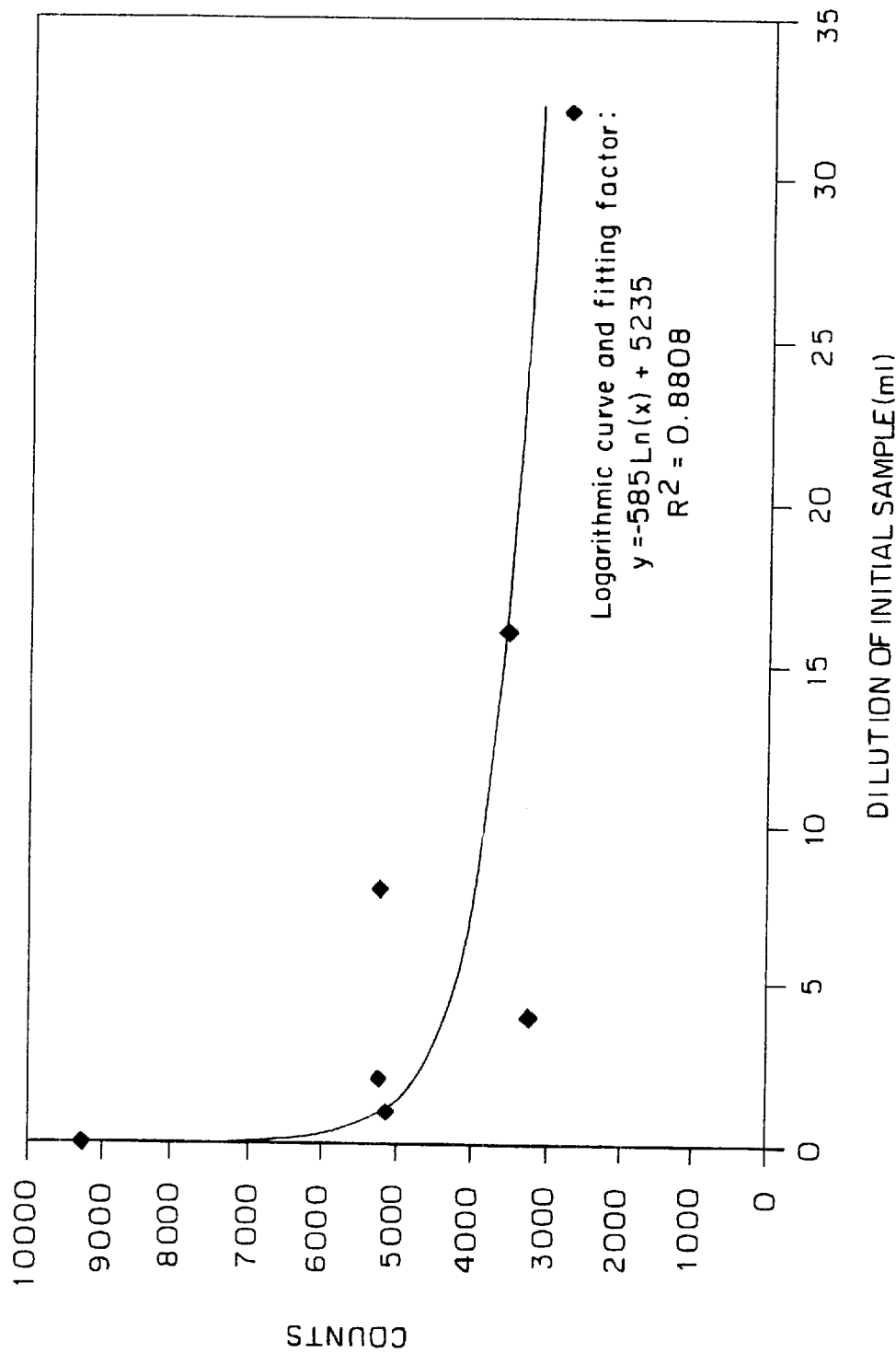
FIG. 21 is a logarithmic curve for variable dilutions of MS2.

The final volume of the solutions processed through the cross flow apparatus is essentially equivalent. The solutions should therefore exhibit the same count rate for MS2, as the initial amount of virus was equal in all cases. The count rates are plotted in FIG. 21, and show a logarithmic decline as the dilutions were increased. The increased dilution's lengthened the contact time with the cross flow filter and subsequently increased the loss of the MS2 bacteriophage through the filter medium.

B.2. In an analysis, the MS2 bacteriophage was able to. pass through the filters of MWCO of 300K and higher daltons and was retained on filters of 100K and less. This result was not expected as the bacteriophage has an approximate size of 2M daltons, and was expected to be retained on the initial filter of 750K MWCO size tested. Collins, et al observed a similar result1, in a report to Koch Membrane Systems, Inc. This study showed the retention of MS2 bacteriophage with MWCO filters of 100K daltons and smaller and the passage of MS2 through a 500K dalton filter. The variable dilution cross flow filtration analysis in this report shows the logarithmic removal of the MS2 from the feed stream, as the solutions were concentrated. The longer the MS2 solution was in contact with the cross flow filter of 750K, the more MS2 was removed from the solution. If the goal of cross flow filtration is to remove salts and other ionic entities, a smaller MWCO filter (such as a 100K) could be used and the MS2 would be retained. However to remove larger macromolecules from a sample of MS2 bacteriophage, a different approach would be needed. A larger MWCO filter (macromolecule dependent) would be used to retain and concentrate the macromolecule while the MS2 bacteriophage is removed in the filtrate stream. The filtrate stream could then be processed separately with a 100K MWCO filter to retain and concentrate the MS2 bacteriophage. The extra step would only add a short period of time to an analysis, as the cross flow filtration process is a fast and efficient filtration.

The MS2 bacteriophage passed through 1M, 750K, 500K and 300K Dalton filters. The phage was retained on the 100K Dalton centrifuge filter. The rate of virus passage is dependent upon back pressure for the tangential flow filters and on gravitational pressure for the centrifuge filters. Variable dilutions with cross flow filtration apparatus and a 750K MWCO filter appear to produce a logarithmic removal of the MS2 during filtration. Implications are clear that a better understanding of molecular weight cut off (MWCO) and how pore sizes are determined and reported need to be further investigated.

C. Characterization of MS2 Bacteriophage

A sample of MS2 bacteriophage provided by the Life Sciences Division at Dugway Proving Ground (DPG) was analyzed and characterized. This sample was 2 ml of purified MS2 bacteriophage at a concentration 1×1014 plaque forming units (pfu)/ml or 10.2 mg protein/ml. This highly purified sample is from Lot #98110.

Figure 22:
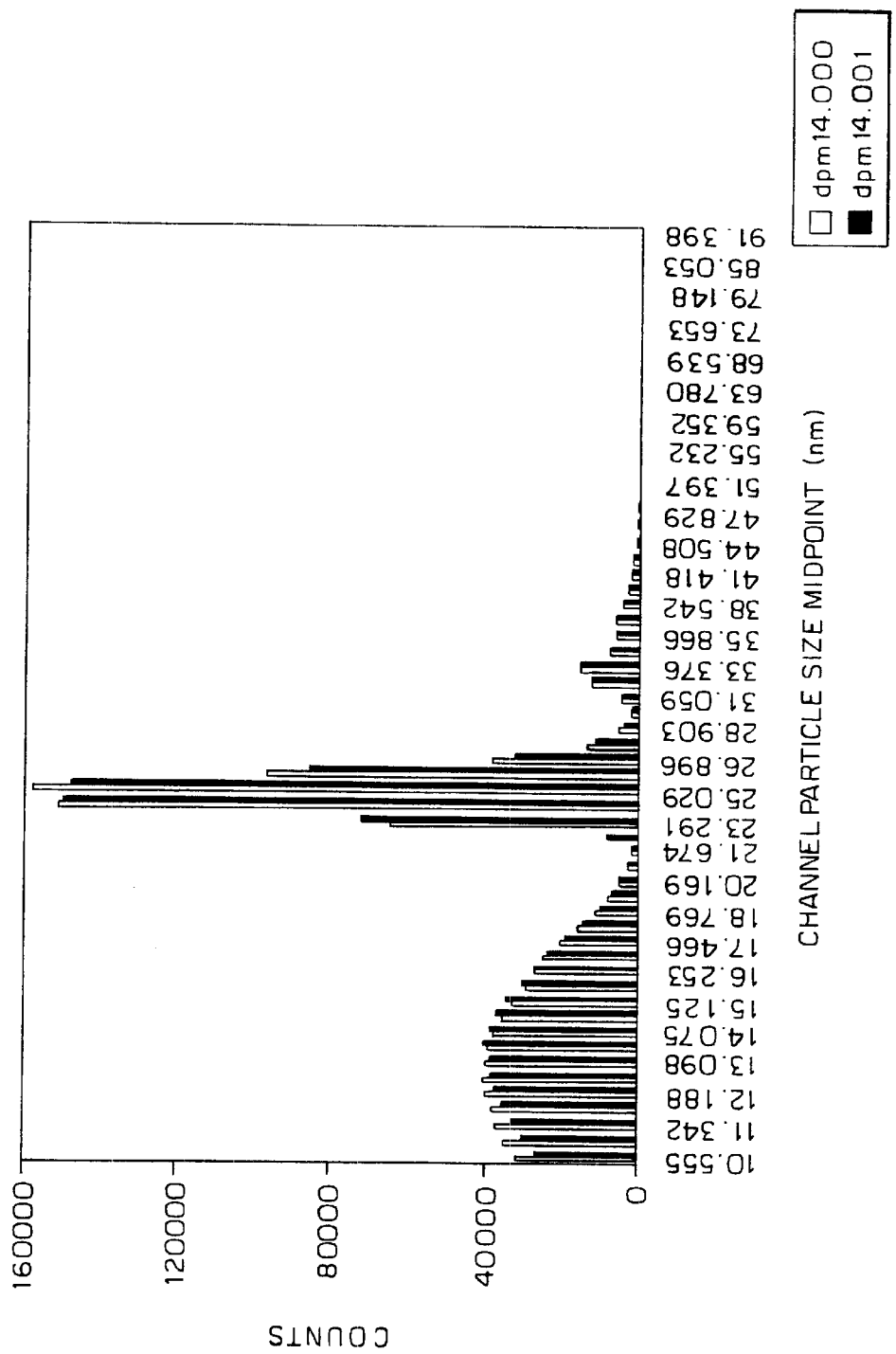
FIG. 22 are results of a GEMMA analysis of MS2 sample, DPM14.
Figure 23:
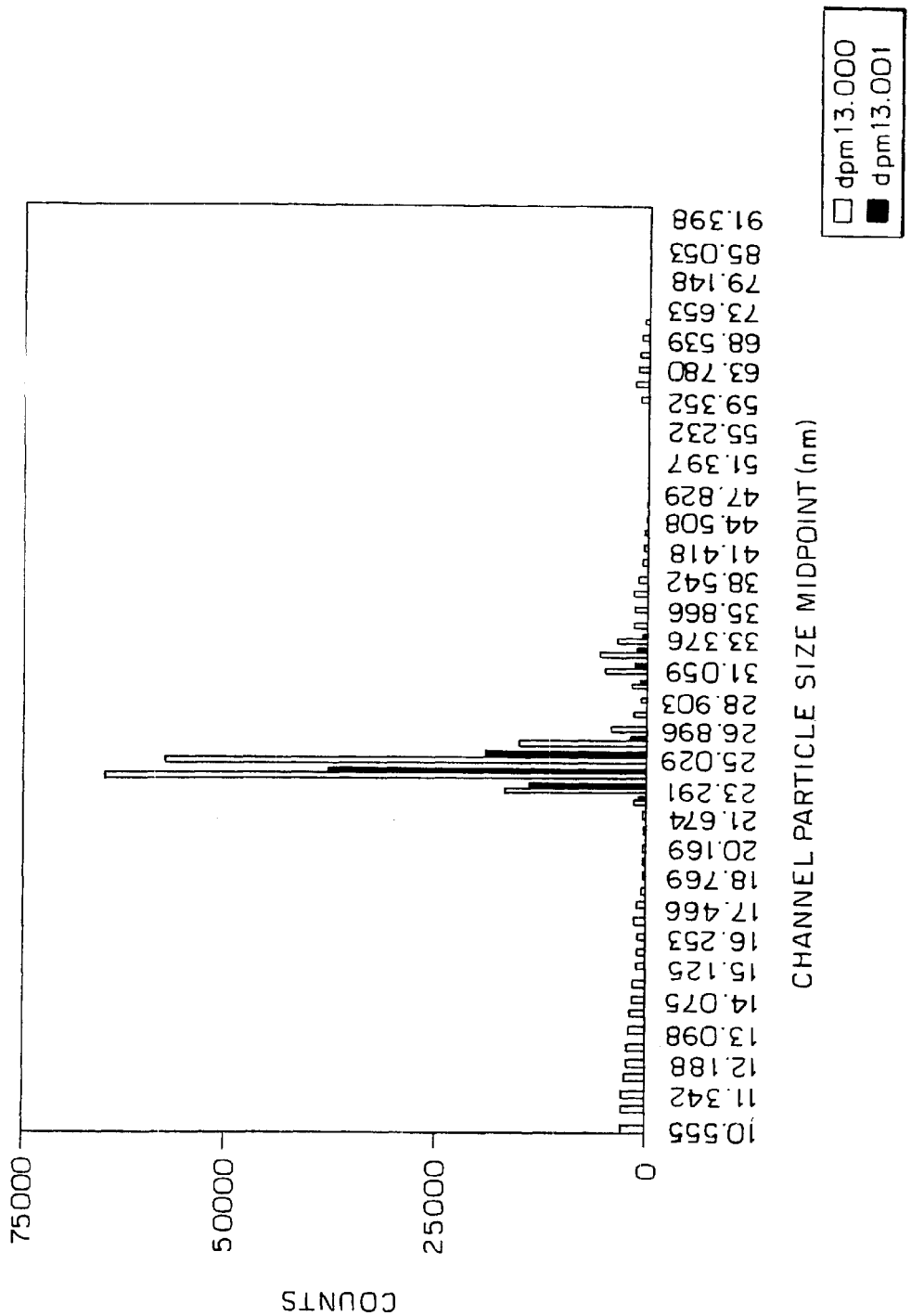
FIG. 23 are results of a GEMMA analysis of MS2 sample, DPM13.
Figure 24:
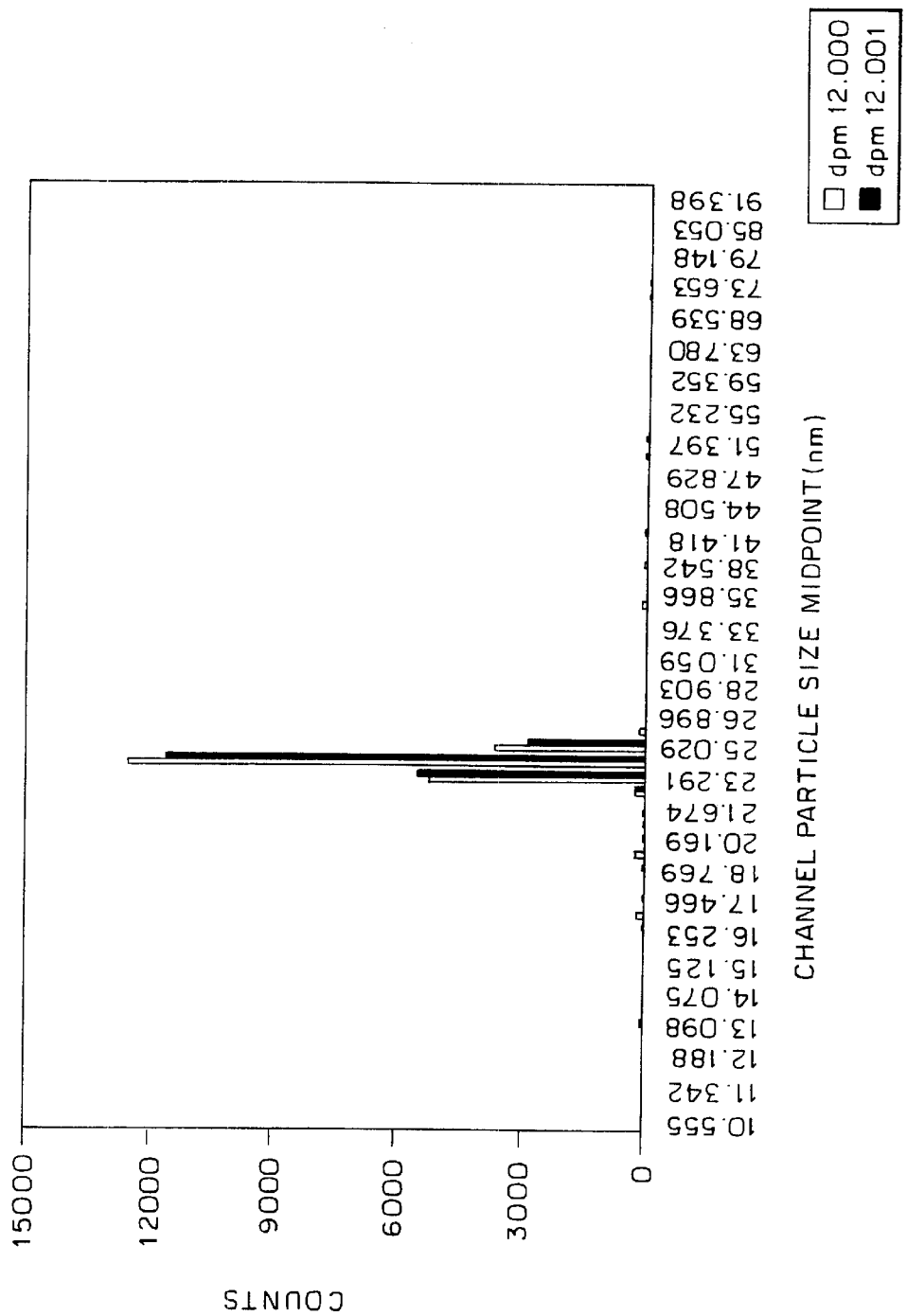
FIG. 24 are results of a GEMMA analysis of MS2 sample, DPM12.
Figure 25:
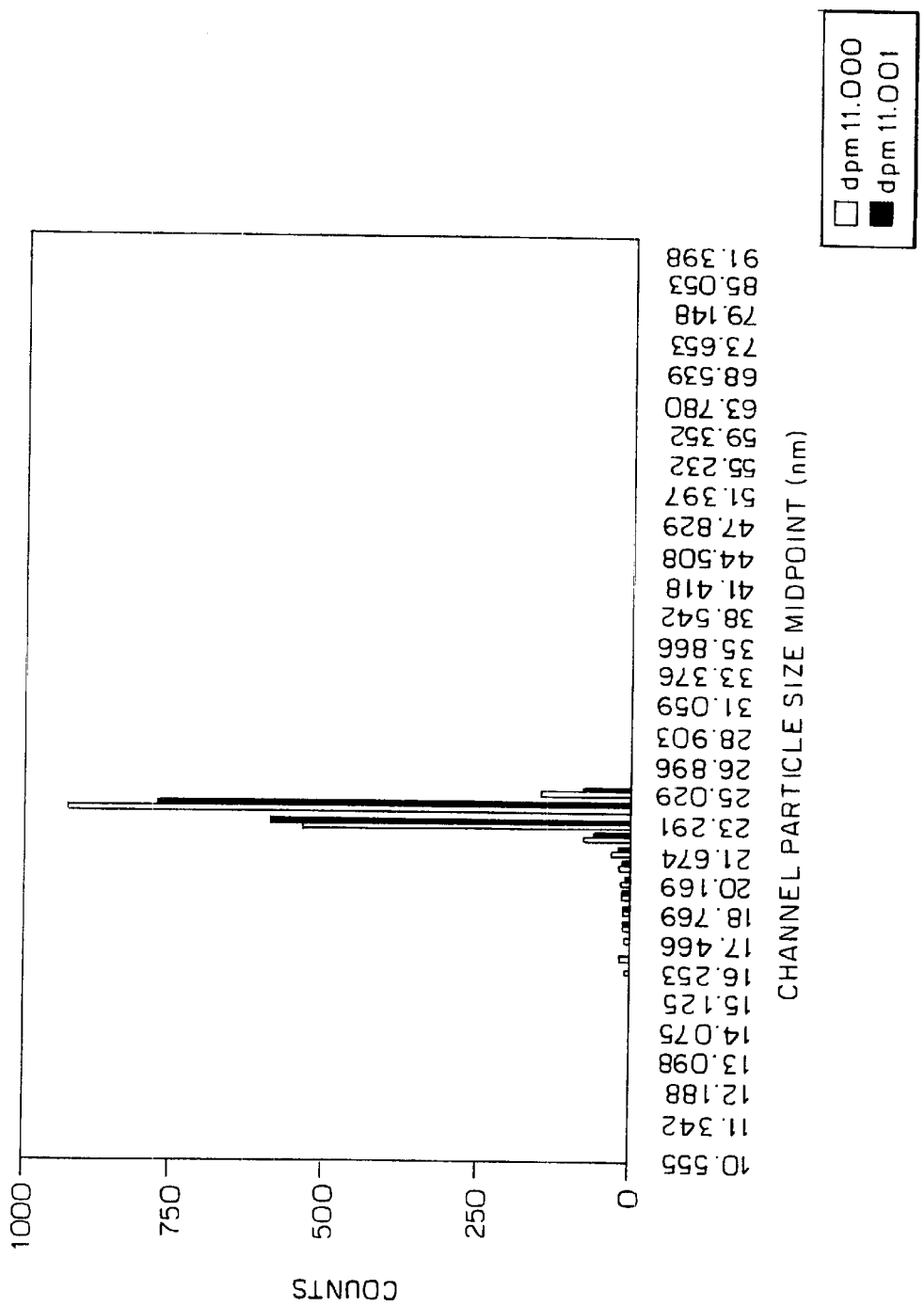
FIG. 25 are results of a GEMMA analysis of MS2 sample, DPM11.
Figure 26:
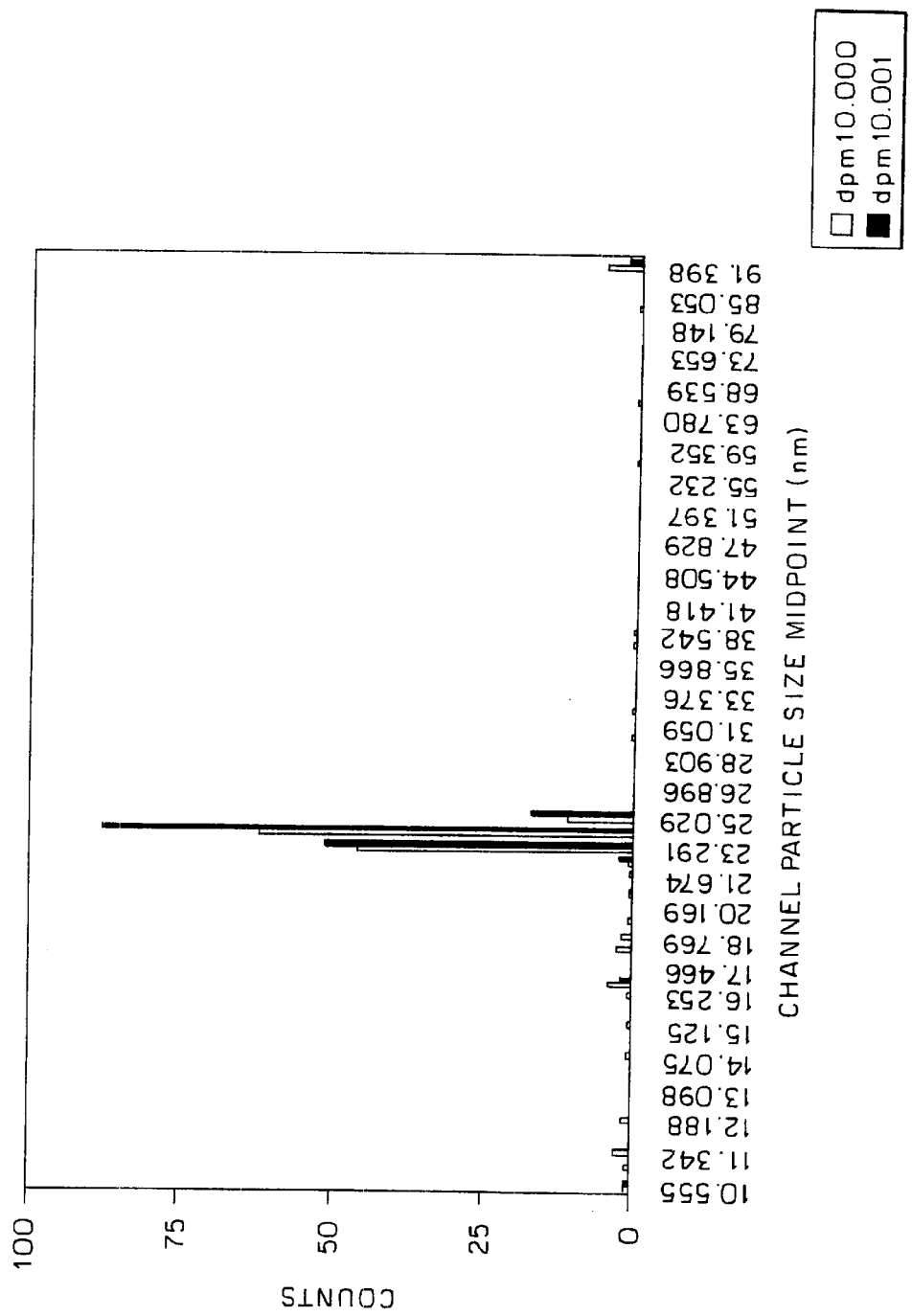
FIG. 26 are results of a GEMMA analysis of a fifth MS2 sample, DPM10.
Figure 27:
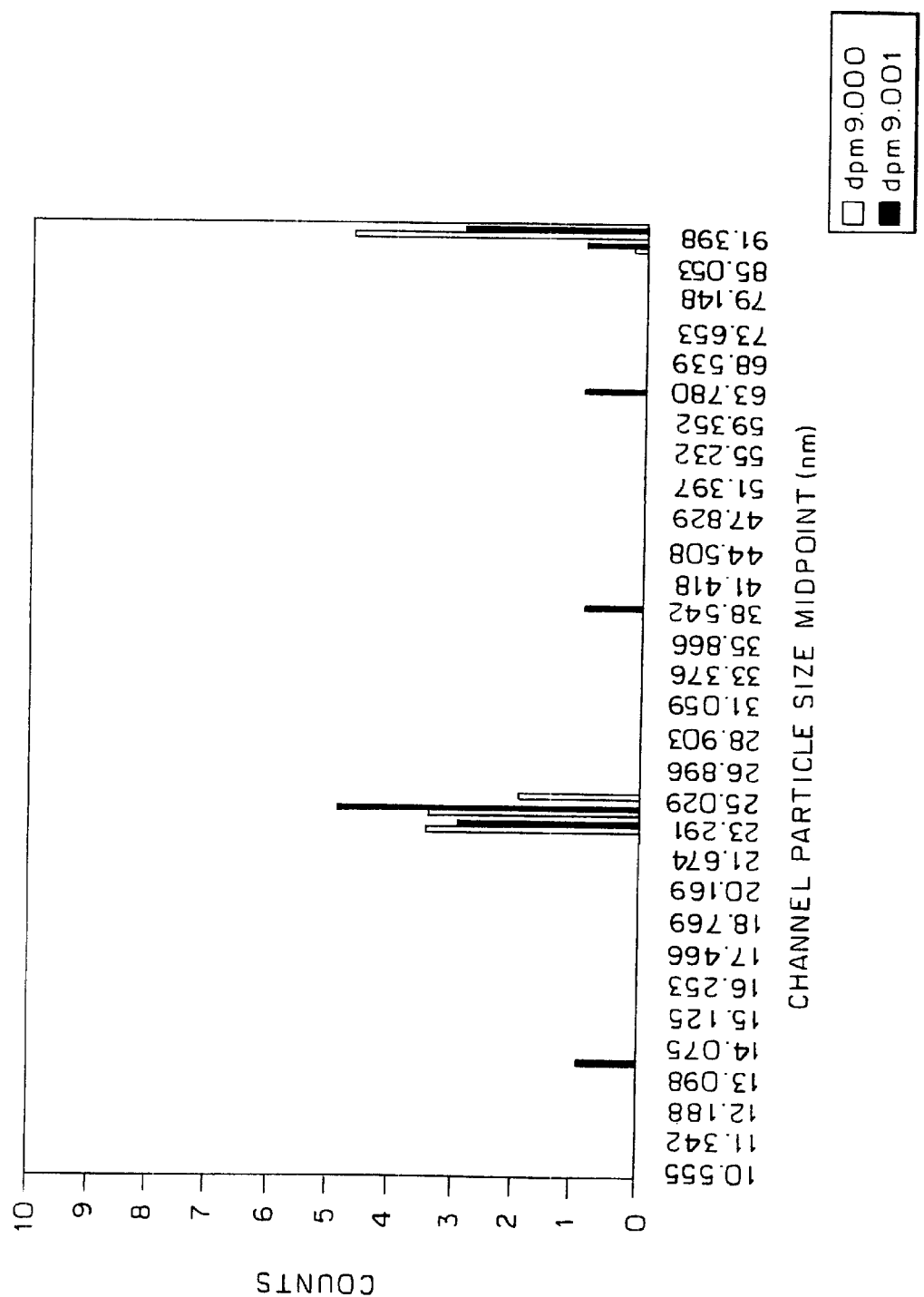
FIG. 27 are results of a GEMMA analysis of a sixth MS2 sample, DPM9.
Figure 28:
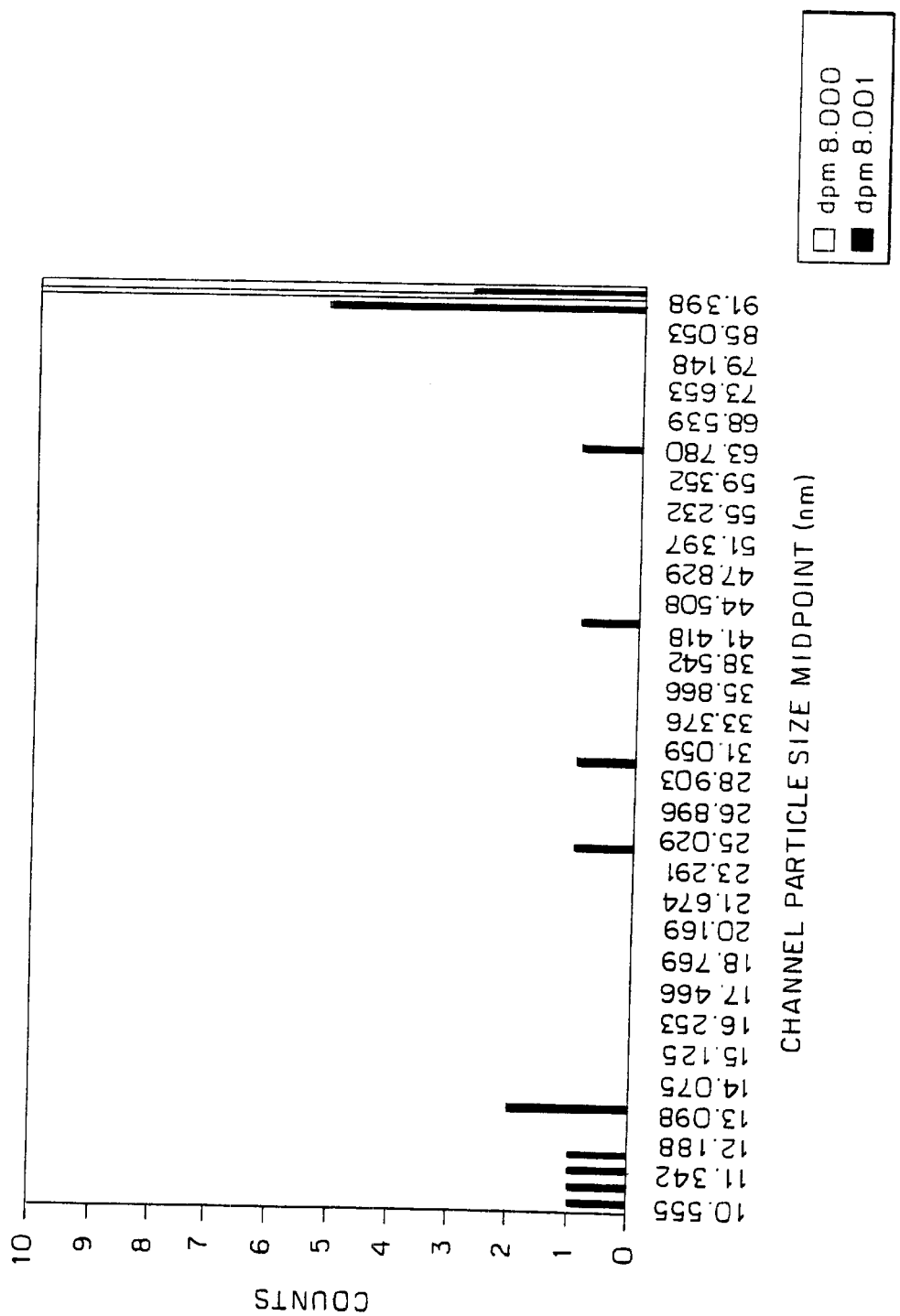
FIG. 28 are results of a GEMMA analysis of a seventh MS2 sample, DPM8.

The MS2 sample was analyzed using the IVDS instrument or more directly the Gas-phase Electrophoretic Mobility Molecular Analyzer (GEMMA) detector which is one stage of the IVDS instrument. The high purity MS2 sample, with 1×1014 pfu/ml (hereafter described as DPM14) was analyzed. The sample of DPM14 was placed neat into the GEMMA analyzer and the results are shown in FIG. 22. The graph shows a very high virus count (over 150,000 counts) as well as other features. MS2 is nominally 24–26 nm in size and this is illustrated in FIG. 22. In fact, the sample as received was difficult to aspirate through the capillary delivery system in the GEMMA.

The size range of 24–26 nm is the expected size for a MS2 bacteriophage. When the difficulty of sampling the neat MS2 sample became apparent, the sample DPM14 was then serially diluted to produce a number of lower concentration samples. That is, an aliquot of DPM14 was diluted 10 fold to produce a sample of MS2 at a concentration of 1×1013 pfu/ml. This sample was named DPM13. The dilutions were all made with a 0.02M solution of ammonium acetate (pH~10), which is required for the electrospray unit. The pH was adjusted to keep the virus from breaking down into its component subunits. Sample DPM13 was then diluted 10 fold, and likewise for the following dilutions. Table 14 lists the samples that were produced by serially dilution of the original sample.

TABLE 14

Serial Dilution Samples of MS2

| | |
|---|---|
| DPM13 | 1×1013 pfu/ml |
| DPM12 | 1×1012 fu/ml |
| DPM11 | 1×1011 pfu/ml |
| DPM10 | 1×1010 pfu/ml |
| DPM9 | 1×109 pfu/ml |
| DPM8 | 1×108 pfu/ml |

FIGS. 23–28 show the resultant GEMMA analysis of the serially diluted MS2 samples. The counts for the serial dilutions were tabulated and are shown in Table 15.

TABLE 15

IVDS Physical Counts for MS2 Samples

Counts in Size Range

| MS2 Sample | 25.946 nm | 25.029 nm | 24.144 nm | 23.291 nm | 22.468 nm |
|---|---|---|---|---|---|
| DPM8 | | | 1 | | |
| DPM9 | | 2 | 5 | 3 | |
| DPM10 | | 17 | 88 | 52 | |
| DPM11 | | 146 | 929 | 541 | 78 |
| DPM12 | 148 | 3613 | 12582 | 5174 | 255 |
| DPM13 | 15216 | 57624 | 65021 | 16893 | 1664 |
| DPM14 | 96995 | 157461 | 150886 | 65389 | 8347 |

The GEMMA detector easily detects MS2 bacteriophage. The virus is consistently detected in the range of 22 to 26 nm. The GEMMA scans also show very low backgrounds away from the MS2 peaks. The action of serially diluting the MS2 did not affect the stability of the bacteriophage in solution. In fact, the addition of ammonium acetate buffer to produce dilutions reduced the background counts. The GEMMA scans of buffer solutions show very low counts, as ammonium acetate is nearly invisible to the detector.

The count rates for the various concentrations of MS2 were tabulated in Table 16. A comparison of the multiplication factor from sample to sample was also tabulated in the table. The lower concentrations display a fairly consistent multiplier and are consistent with the target dilutions. As the concentrations increase, the multiplier appears to decrease in magnitude. As was noted above, the as received sample, DPM14, was difficult to aspirate into the GEMMA detector. This sample is very concentrated and this appears to interfere with the analysis. The reduction in the multiplier may be caused by the agglomeration of particles as they flow through the Condensate Particle Counter (CPC) in the GEMMA unit. This agglomeration would lower the amount of particles counted and reduce the multiplier. It would appear that a count rate over 100,000 counts in a few adjacent channels, with a virus in this size range of 25 nm, is approaching an upper limit to concentrations that can be analyzed in the detector. This is easily remedied by simply diluting a sample to less than 100,000 counts in adjacent channels.

TABLE 16

5/28 Numerical Analysis of MS2 Peak Count Information

| MS2 Sample | Sum of size range | Multiplier from sample to sample |
|---|---|---|
| DPM8 | 1 | — |
| DPM9 | 10 | 10.0 |
| DPM10 | 157 | 15.7 |
| DPM11 | 1694 | 10.8 |
| DPM12 | 21772 | 12.9 |
| DPM13 | 156418 | 7.2 |
| DPM14 | 479078 | 3.1 |

The actual sensitivity of the GEMMA detector was not in question in this study. The presented solution to the detector can be further concentrated to allow for the analysis of samples that appear to be too dilute. The sample DPM8 could be concentrated from one ml, the original volume, to 10 $\mu$l. This would then present the GEMMA detector with a sample that would generate a graph with ~100 counts in a scan. The number of viruses that can be detected by the GEMMA is very low, on the order of 10 viruses, and therefore the ability to detect viruses is only a function of the presented solution concentration. A further example was a simple experiment where a few thousand viruses were measured into 500 ml of water. The water sample was concentrated through the Ultrafilter unit and nearly 800 viruses were counted by the GEMMA. The limiting factor for analysis is the ability to further concentrate a liquid solution while still being able to effectively handle the solution without losing it due the handling problems associated with tiny volumes.

The sample of MS2 bacteriophage received from the Life Sciences Division at Dugway Proving Ground was a very pure and concentrated sample. No other viruses were detected. The sample responded well to serial dilutions and was stable in the ammonium acetate buffer. This technique is a simple method to test the purity of any virus preparation since the IVDS instrument is not limited to any particular virus.

It should be understood that the foregoing summary, detailed description, and drawings of the invention are not intended to be limiting, but are only exemplary of the inventive features which are defined in the claims.

What is claimed is:

1. An apparatus for detecting the presence of different size groups of submicron sized particles in a sample taken from the environment, comprising:

(a) a collecting means for collecting a sample from the environment;

(b) means for detecting the particles in the collected sample, the detecting means comprising: an electrospray assembly having an electrospray capillary which receives the collected sample from the collecting means, a differential mobility analyzer which receives the output from the electrospray; and a condensation particle counter means for counting the number of particles received from the differential mobility analyzer.

2. The system of claim 1, wherein the collecting means comprises an ultracentrifuge for density-gradient ultracentifugation of the sample so that the particles are separated according to their density.

3. The apparatus of claim 2, wherein the ultracentrifuge has an ultracentrifuge rotor having a rotational speed of about 60,000 revolutions per minute.

4. The apparatus of claim 1, wherein the collecting means comprises a collector having means for liquid scrubbing a collected fluid sample of aerosol and gaseous materials containing the particles and a means for reducing the size of solid materials in the fluid sample.

5. The apparatus of claim 4, wherein the collector includes a water injector means for scrubbing a collected fluid sample of aerosol and gaseous materials containing the particles, and the collecting means further comprising a holding tank having a homogenizer connected to the collector for receiving the scrubbed fluid sample and for reducing the size of solid materials in the fluid sample.

6. The apparatus of claim 1, wherein the collecting means comprises a liquid sample collector.

7. The apparatus of claim 1, wherein the collecting means collects samples of airborne materials containing the particles, wherein the materials have size ranges of from about 2 to about 10 microns.

8. The apparatus of claim 7, wherein the particles comprise viruses, prions, macromolecules, proteins, satellite and virus fragments having size ranges of from about 10 to about 350 nanometers.

9. The apparatus of claim 1, wherein the collecting means samples air at a rate of from about 100 to about 4,000 liters per minute.

10. The apparatus of claim 1, wherein the collecting means collects a sample containing particles having a density from about 1.175 grams per milliliter to about 1.5 grams per milliliter, a size from about 10 nanometers to about 350 nanometers and a level of nonviral impurities of less than about 100 parts per million.

11. The apparatus of claim 1, further comprising conduit means connected to the collecting means and the means for detecting the particles for conveying the fluid sample from the collecting means to the means for detecting the particles.

12. The apparatus of claim 1, wherein the particles have size ranges of from about 10 to about 350 nanometers and are selected from the group consisting of viruses, prions, macromolecules, proteins, satellite and virus fragments.

13. The apparatus of claim 1, further comprising a biomarker means connected to the collecting means for adding a biomarker of known size and concentration to the collected sample for including in the output of the condensation particle counter means an output of known size and concentration for reference with the size and concentration of the particles that are counted.

14. An apparatus for detecting the presence of different size groups of submicron sized particles in a sample taken from the environment, comprising:

(a) a collecting means for collecting a sample containing the particles from the environment; and (b) detecting means connected to the collecting means for detecting the particles in the collected sample, the detecting means comprising a means for placing a charge on the particles, a means for separating the charged particles based on the size of the particles and a means for counting the number of separated particles in the collected sample.

15. The apparatus of claim 14, further comprising a biomarker means connected to the collecting means for adding biomarker particles of known size and concentration to the collected sample for including in the counted number of separated particles in the collected sample the biomarker particles of known size and concentration.

16. A method for detecting the presence of submicron size particles in a sample taken from the environment, comprising the steps of:
(a) collecting a fluid sample containing submicron size particles comprising viruses, prions, macromolecules, proteins, satellite and virus fragments;

(b) directing the collected fluid sample to an electrospray assembly having an electrospray capillary for introducing droplets of the fluid sample containing the submicron size particles into an electrospray assembly under the influence of an electric field;

(c) directing the output from the electrospray assembly to a differential mobility analyzer for separating the submicron size particles according to size; and (d) directing the separated submicron size particles from the differential mobility analyzer to a condensation particle counter for counting the number of submicron size particles in the fluid sample.

17. The method of claim 16, wherein the collecting step collects samples containing submicron size particles having sizes ranging from about 10 to about 350 nanometers.

18. The method of claim 16, further comprising the step of adding a biomarker of known size and concentration to the collected sample for including in the output of the condensation particle counter an output of known size and concentration for reference with the submicron size particles that are counted in a sample.

19. A method for detecting the presence of submicron size particles in a sample taken from the environment, comprising the steps of:

(a) collecting a sample containing the submicron size particles;

(b) detecting the submicron size particles in the collected sample by placing a charge on the submicron size particles, separating the charged submicron size particles based on the size of the submicron size particles, and counting the number of separated submicron size particles in the sample.

20. The method of claim 19, further comprising the step of adding biomarker particles of known size and concentration to the collected sample for including in the counted submicron size particles the biomarker particles of known size and concentration.

* * * * *